United States Patent [19]

Takishita et al.

[11] Patent Number: 5,117,697
[45] Date of Patent: Jun. 2, 1992

[54] ULTRASONIC FLAW DETECTOR

[75] Inventors: Yoshihiko Takishita, Ibaraki; Souji Sasaki, Hitachi, both of Japan

[73] Assignee: Hitachi Construction Machinery Co., Ltd., Tokyo, Japan

[21] Appl. No.: 476,429
[22] PCT Filed: Sep. 5, 1989
[86] PCT No.: PCT/JP89/00913
   § 371 Date: May 25, 1990
   § 102(e) Date: May 25, 1990
[87] PCT Pub. No.: WO90/02945
   PCT Pub. Date: Mar. 22, 1990

[30] Foreign Application Priority Data
   Sep. 5, 1988 [JP] Japan .................. 1-220458

[51] Int. Cl.$^5$ ............................................ G01N 29/04
[52] U.S. Cl. ........................................................ 73/626
[58] Field of Search ............... 73/626; 128/661.01; 367/105

[56] References Cited

U.S. PATENT DOCUMENTS 4,135,140  1/1979  Buchner ........................... 73/626
4,589,284  5/1986  Breimesser et al. .............. 73/626

FOREIGN PATENT DOCUMENTS 59-95262   6/1984  Japan .
62-191757  8/1987  Japan .
1-197649   8/1989  Japan .

OTHER PUBLICATIONS

Patent Abstract of Japan, vol. 8, No. 242 (p. 311)(1697) Nov. 7, 1984 & JP-A-59 116542 (Kobe Seikosho K.K.) Jul. 5, 1984.
Patent Abstracts of Japan, vol. 7, No. 260 (p. 237)(1405) Nov. 18, 1983, & JP-A-58 143265 (Nihon Denpa Kogyo K.K.) Aug. 25, 1983.
Patent Abstracts of Japan, vol. 7, No. 98 (p. 664) Aug. 22, 1987 & JP-A-62 191757 (Nippon Steel Corp.) Aug. 22, 1987.

Primary Examiner—John E. Chapman
Attorney, Agent, or Firm—Wegner, Cantor, Mueller & Player

[57] ABSTRACT

The present invention is directed to an ultrasonic flaw detector for inspecting the surface condition of a specimen or the existence or non-existence of one or more internal defects in the specimen by scanning the specimen with ultrasonic waves and analyzing waves reflected by the specimen. The ultrasonic flaw detector includes a number of array elements arranged in a line. The ultrasonic beam scanning of a specimen is performed by vibrating plural ones of the array elements to form a single ultrasonic beam and shifting vibration of the array elements one by one. Array elements are divided into plural blocks by a block selector. Ultrasonic scanning is simultaneously conducted in the respective blocks. Omission of ultrasonic scanning between each two adjacent blocks is avoided by setting the blocks to overlap at adjacent sections and causing, with a switch, the array elements in the overlapped sections to belong to one of the blocks at a certain time point to take part in ultrasonic scanning and to the other block at another time point to take part in ultrasonic scanning. Owing to this construction, ultrasonic scanning can be performed quickly.

3 Claims, 20 Drawing Sheets

FIG. 12

|  | Symbol/General Formula | Example |
|---|---|---|
| Total number of array elements | N | 128 |
| Number of vibrated elements | M | 8 |
| Number of simultaneous beams | K | 4 |
| Total number of beams | N − M + 1 | 121 |
| Number of electronic scanning operations | N / K | 32 |
| Number of outputs from distributor | N / M | 16 |
| Number of inputs to adder | N / (M · K) + 1 | 5 |
| Total number of address | M · K | 32 |
| Total number of switches | M ( K − 1 ) | 24 |

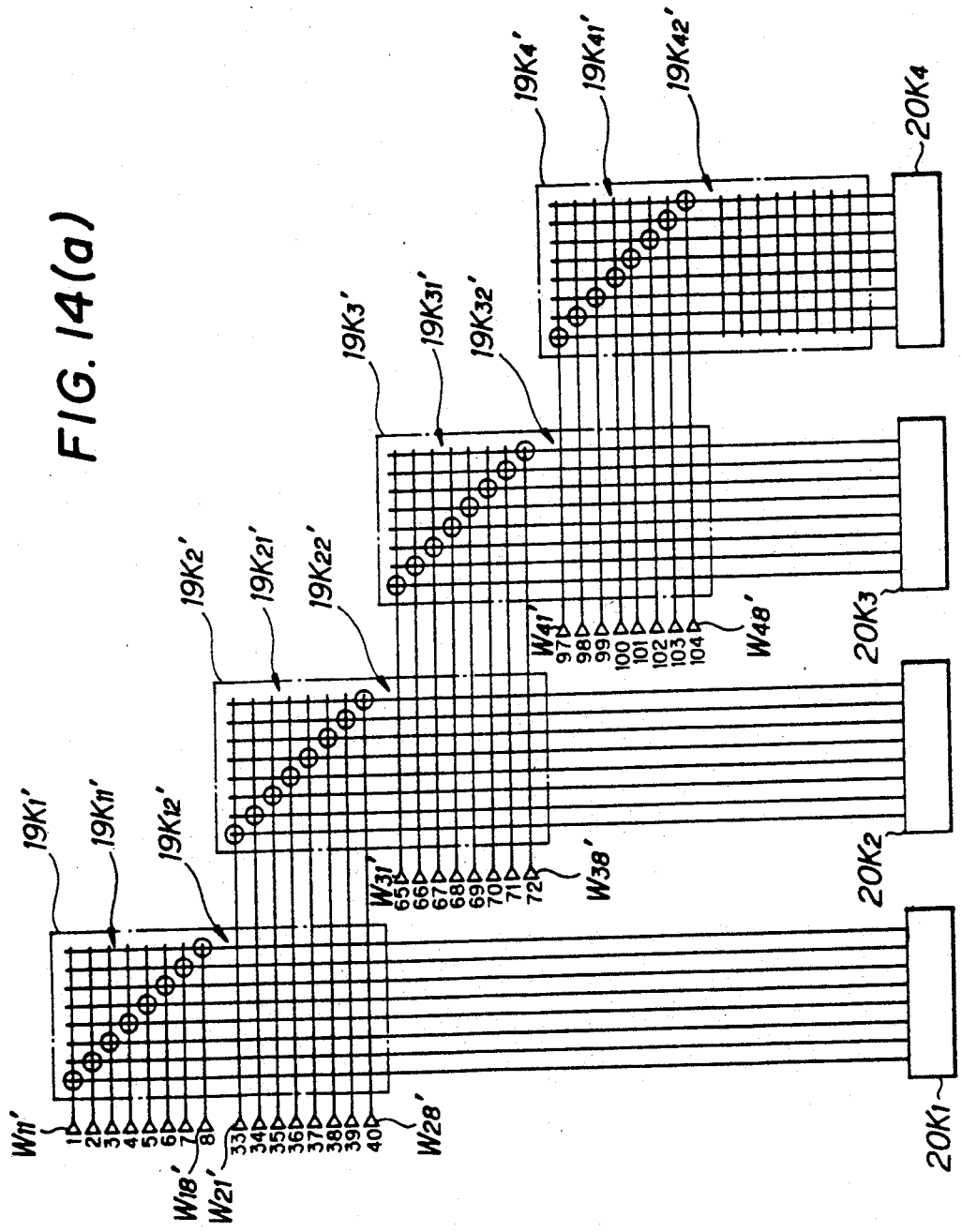

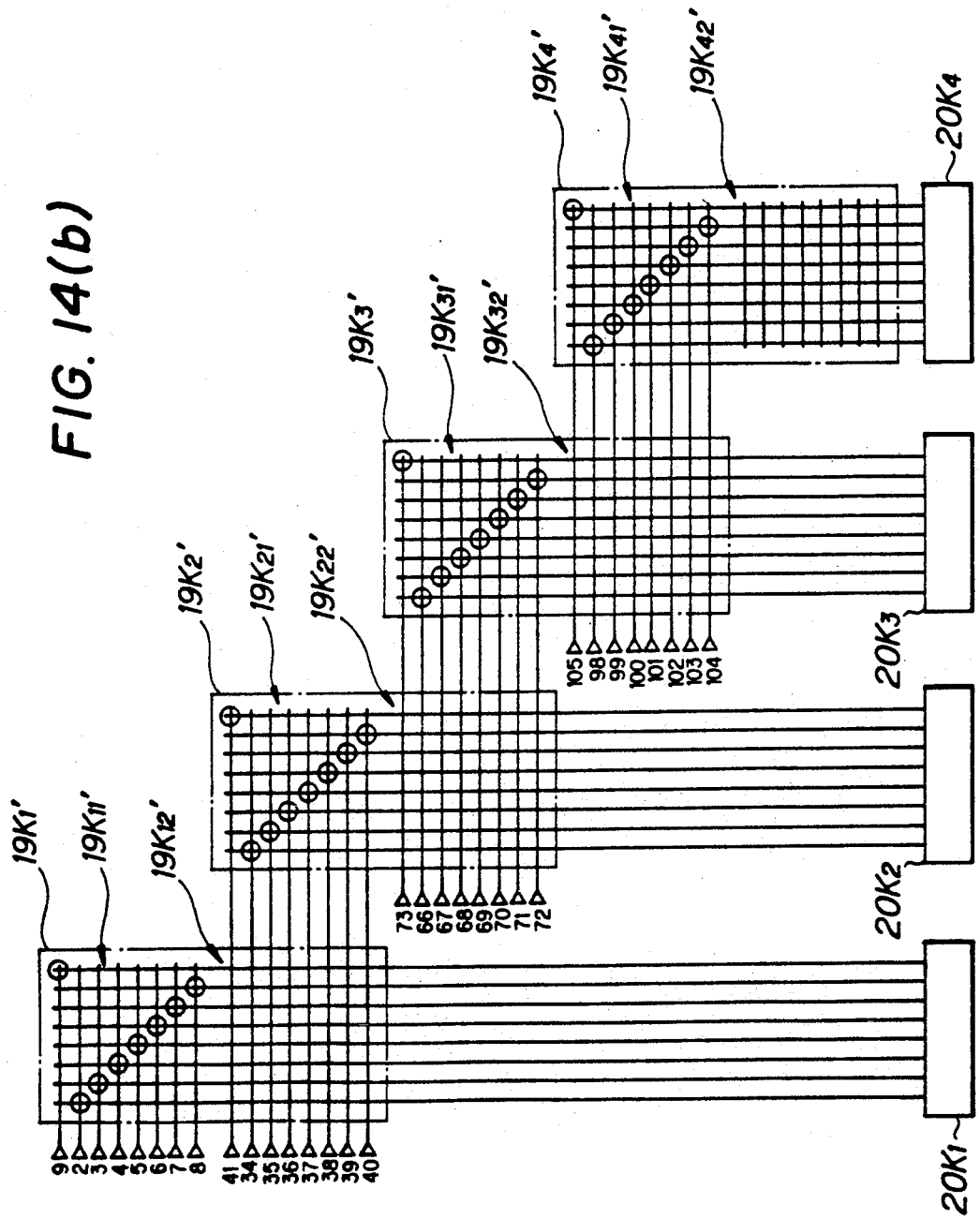

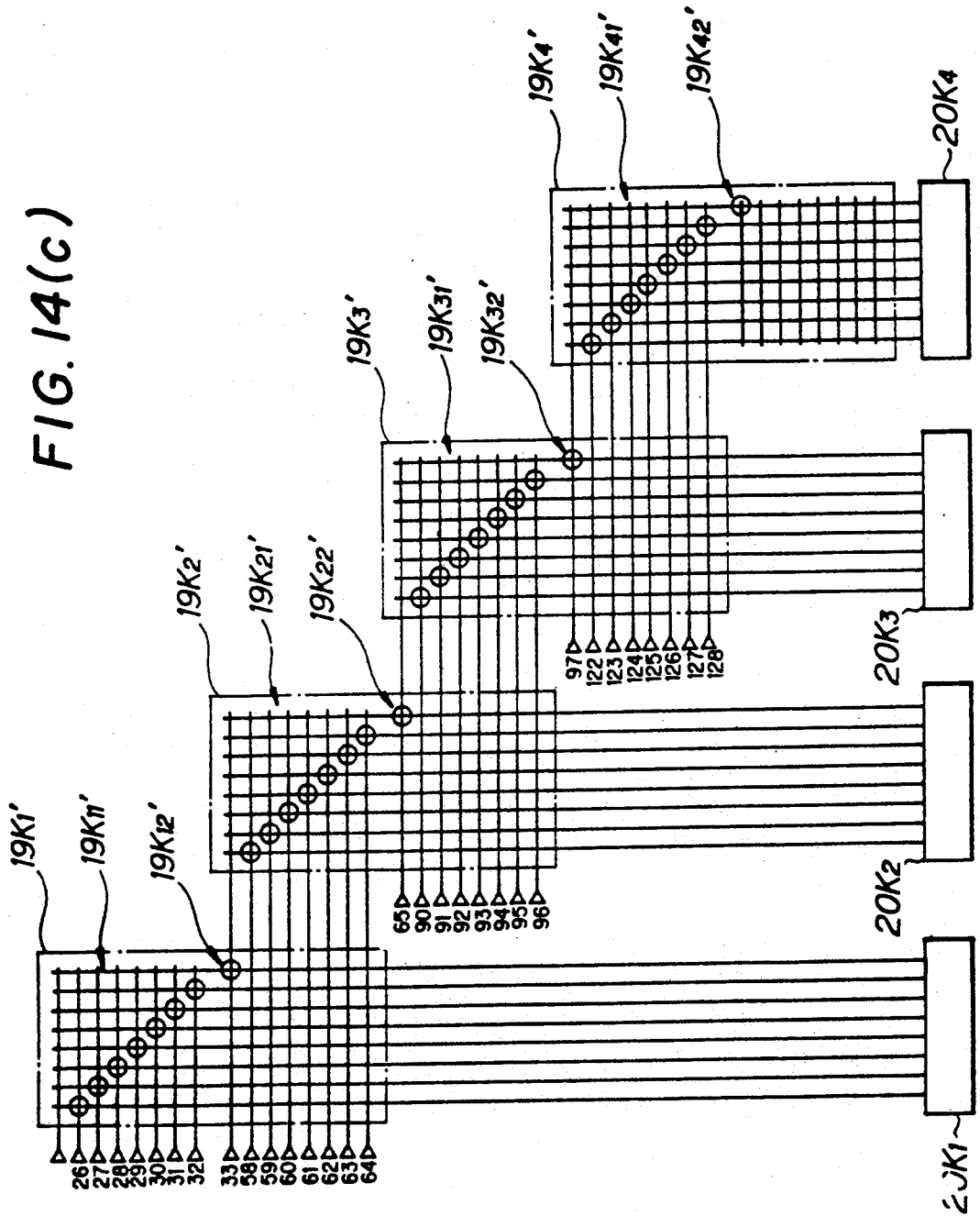

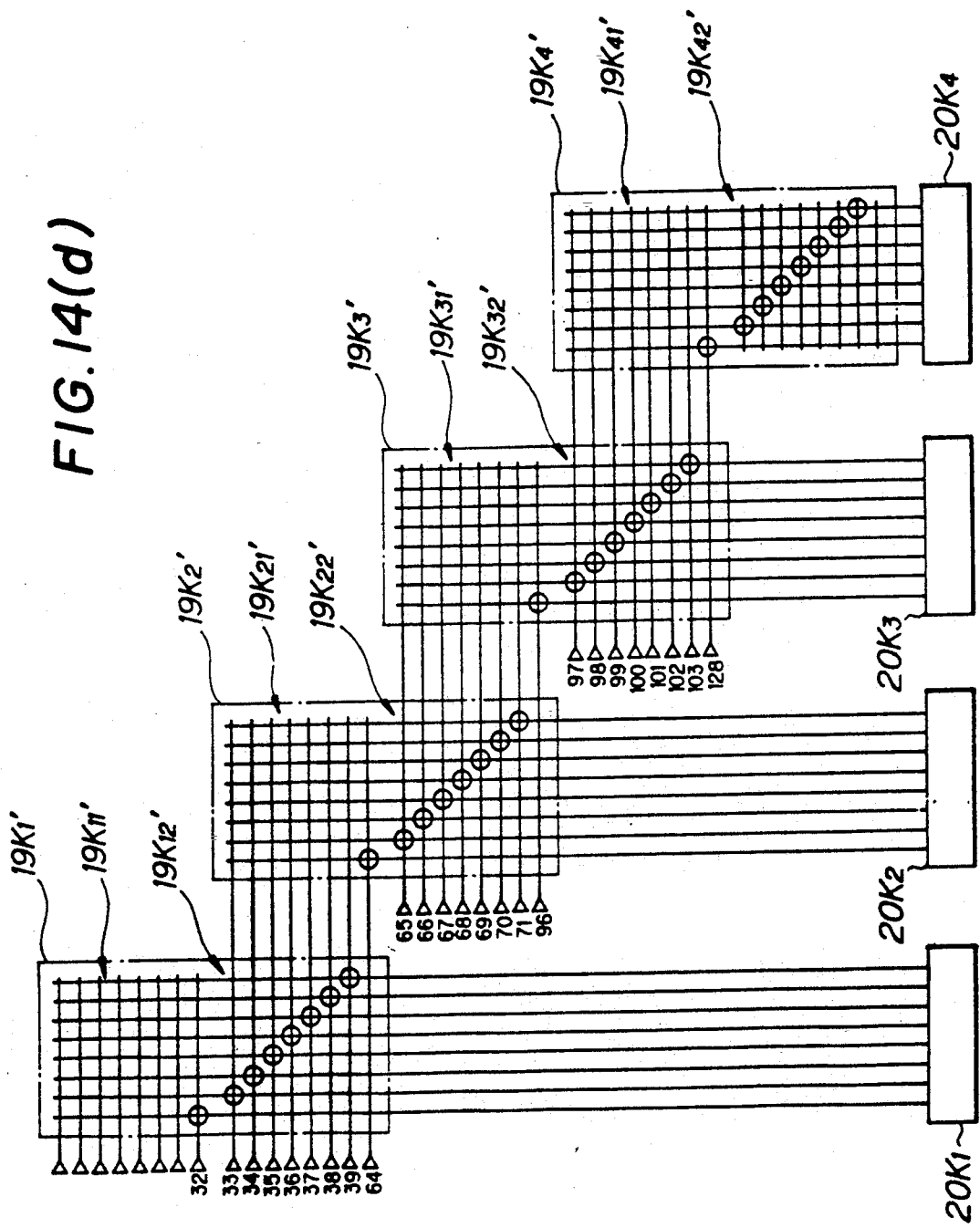

ULTRASONIC FLAW DETECTOR

TECHNICAL FIELD

The present invention relates to an ultrasonic flaw detector for inspecting the surface condition of a specimen or the existence or non-existence of one or more internal defects in the specimen by radiating ultrasonic waves to scan the specimen and then analyzing waves reflected by the specimen.

BACKGROUND ART

Ultrasonic flaw detectors can detect internal defects of specimens without destruction of the specimens and are employed in many fields. The existence or non-existence of a defect inside a specimen is checked over a predetermined area of the specimen in many instances. In this case, the inspection is conducted by scanning the above-described area of the specimen with ultrasonic waves radiated from a probe. Actually employed as such a probe includes an array probe constructed of many piezoelectric elements arranged in a line. An ultrasonic flaw detector making use of such an array probe will hereinafter be described.

FIG. 1 is a perspective view of a scanner unit of the conventional ultrasonic flaw detector. FIGS. 2(a) and 2(b) are plan and side views of an array probe, respectively. In each of the drawings, there are shown a water tank 1 for inspection, water 2 charged in the water tank 1, and a specimen 3 placed on the bottom wall of the water tank 1. Designated at numeral 4 is a scanner, which is constructed of the following members: a scanner table 5 on which the water tank 1 is mounted, frames 6 fixed on the scanner table 5, an arm 7 extending between the frames 6, a holder 8 mounted on the arm 7, a pole 9 pendant from the holder 8, and an array probe 10. The frames 6 can move the arm 7 in the direction of Y-axis by an unillustrated mechanism, while the arm 7 can move the holder 8 in the direction of Y-axis by a mechanism which is free of illustration. Further, the holder 8 can move the array probe 10 in the direction of Z-axis (the direction perpendicular to X-axis and also to Y-axis) in association with the pole 9 by means of a mechanism (not shown).

The array probe 10 is constructed of a number of minute piezoelectric elements (hereinafter called "array elements") arranged in a line. The direction of arrangement of the array elements is in conformance with the direction of X-axis. Whenever a pulse is applied, each array element radiates an ultrasonic wave and then converts a reflected wave of the ultrasonic wave by the specimen 3 to a corresponding electrical signal. The individual array elements are indicated by numerals $10_1$–$10_n$ in FIGS. 2(a) and 2(b), in which dots indicate points of sampling. Symbol YP indicates the sampling pitch in the direction of Y-axis, while symbol XP represents the sampling pitch in the direction of X-axis. In addition, symbol AP shows the pitch between the adjacent array elements $10_1$–$10_n$. Designated at numeral 11 is a casing in which the array probe 10, etc. are accommodated.

Here, the function of the array probe 10 shown in each of the above drawings is described in brief with reference to FIGS. 3(a) and 3(b). In FIG. 3(a), there are illustrated array elements $T_1$–$T_9$ arranged in a line, delay elements $D_1$–$D_9$ connected to the respective array elements $T_1$–$T_9$, and pulses p to be inputted to the respective array elements $T_1$–$T_9$. The delay elements $D_1,D_9$ have been set at the same delay time ($t_{19}$). Likewise, the delay elements $D_2,D_8$ at the same delay time ($t_{28}$), the delay elements $D_3,D_7$ at the same delay time ($t_{37}$), and the delay elements $D_4,D_6$ at the same delay time ($t_{46}$). The relationship among the delay times thus set can be expressed by the following inequality:

$$t_{19} < t_{28} < t_{37} < t_{46} < t_5 \qquad (1)$$

where $t_5$ stands for the delay time of the delay element $D_5$.

Now, the delay times of the individual delay elements $D_{1-9}$ are set at desired values while maintaining the relationship of the inequality (1), and the pulses p are inputted. From the array elements $T_1$–$T_9$, ultrasonic waves are then radiated in accordance with the delay times so set, i.e., first from the array elements $T_1,T_9$ and last from the array element $T_5$. The ultrasonic waves radiated in the above manner then advance radially and inwardly, so that there is a point where the maximum amplitudes of oscillations of the ultrasonic waves radiated from the respective array elements all coincide. This point is indicated by letter F in FIG. 3(a). Since the magnitude of the resulting ultrasonic wave is far greater at the point F compared to that of ultrasonic wave at any other point, the ultrasonic waves from the respective array elements $T_1$–$T_9$ become as if converged at the point F as indicated by dashed lines. In other words, the application of suitable delays to the radiation of ultrasonic waves from respective array elements arranged in a line can develop a situation similar to the convergence of such ultrasonic waves at the point F. This point F will therefore be called "the point of convergence". Described further, the array elements $T_1$–$T_9$ outputs an ultrasonic beam B which converges at the point F of convergence as indicated by the dashed lines. If the respective delay times are set shorter than the above-described delay times while maintaining the relationship of the inequality (1), the point F of convergence is shifted to a farther point F' of convergence as indicated by alternate long and short dash lines (beam B'). It is therefore possible to select the position of the point of convergence by adjusting the delay times of the individual delay elements $D_1$–$D_9$. When used for the inspection of the specimen 3, the depth of the point of inspection can be selected.

FIG. 3(b) is a schematic illustration of the function of the array probe 10 shown in FIGS. 2(a) and 2(b). In the drawing, numerals $10_1$–$10_n$ indicate the same array elements as depicted in FIG. 2(a). Delay elements are connected to the individual array elements $10_1$–$10_n$ although not illustrated. In the illustrated example, m pieces of array elements $10_1$–$10_m$ are first selected and the delay times of ultrasonic waves to be radiated from the array elements are set appropriately, whereby the ultrasonic waves are apparently caused to converge at one point of convergence as described above. In FIG. 3(b), this point of convergence and an apparent ultrasonic beam are indicated by symbols $F_1$ and $B_1$, respectively. Next, the vibration of array elements is shifted by one element so that delay times of the same pattern as the delay times applied to the array elements $10_1$–$10_m$ in the preceding vibration are applied to the m pieces of array elements $10_2$–$10_{m+1}$. For this vibration, the point of convergence is indicated by symbol $F_2$ while the resulting ultrasonic beam is designated by symbol $B_2$. Thereafter, the vibration of array elements is shifted successively one by one. The array elements $10_{n-m+1}$-$10_n$ are finally selected, to which delay times of the same pattern are applied to obtain a point $F_{n-m+1}$ of convergence and an ultrasonic beam $B_{n-m+1}$. As a consequence, ultrasonic scanning can be performed from the point $F_1$ of convergence to the point $F_{n-m+1}$ of convergence by the array probe 10 in the manner described above. The scanning will hereinafter be called "electronic scanning" as it is electronically performed at a high speed. In FIG. 3(b), AP and SP indicate the pitch of the array elements and the sampling pitch, respectively. They are equal to each other in the illustrated example.

A description will next be made of a control unit of the ultrasonic flaw detector making use of the array probe described above. In this description, assume by way of example that an area of a specimen, said area being to be inspected, has a length of 120 mm in the direction of X-axis, the array probe 10 is equipped with 128 array elements, the pitch of the array elements is 1 mm, eight array elements are vibrated at the same time, and the scanning of the specimen is performed with 121 beams in the direction of X-axis. FIG 4 shows the arrangement of the above array elements, in which there are illustrated the array probe 10, array elements $10_1$-$10_{128}$ and ultrasonic beams $B_1$-$B_{121}$. The individual array elements $10_1$-$10_{128}$ are indicated by numerals 1-128 in the drawing. The control unit is indicated at numeral 11.

FIG. 5 is a block diagram of the control unit 11 shown in FIG. 4. In the drawing, numeral 10 indicates the array probe. Designated at numeral 12 is a microprocessor, while numeral 13 indicates a transmission delay circuit for delaying, by predetermined times, vibration of the individual array elements which are adapted to give off ultrasonic beams $B_1$-$B_{121}$, respectively. Only one transmission delay circuit 13 is provided for the individual ultrasonic beams $B_1$-$B_{121}$. There are also illustrated a matrix circuit 14 and a distributor 15. They are provided to use the transmission delay circuit 13 commonly for the respective ultrasonic beams $B_1$-$B_{121}$. Designated at numeral 16 is a transmit-receive circuit, which outputs vibrating pulses to the individual array elements $10_1$-$10_{128}$ of the array probe 10 and also receives signals of reflection waves from the individual array elements $10_1$-$10_{128}$. The constructions of the matrix circuit 14, distributor 15 and transmit-receive circuit 16 will be described in further detail with reference to FIG. 6, FIG. 7 and FIG. 8. Designated at numeral 17 is a shift register, which serves to successively connect the transmit-receive circuit 16 to groups of eight array elements, each group being to be employed to form a single ultrasonic beam. Numeral 18 indicates an adder having the same construction as the distributor 15 except that the input and output are opposite, and numeral 19 designates a matrix circuit of the same construction as the matrix circuit 14. Designated at numeral 20 is a waveform adder, which brings into coincidence the phases of eight signals outputted from the matrix circuit, followed by the addition. Each output of the waveform adder 20 is processed suitably and then displayed in a desired mode. Based on the output thus displayed, it is determined whether the specimen contains a defect or not.

The operation of the control circuit 11 will next be described with successive reference to FIG. 6, FIG. 7 and FIG. 8.

(I) Operations of the Transmission Delay Circuit 13 and Matrix Circuit 14

FIG. 6 is a circuit diagram around the matrix circuit 14, in which elements identical to their corresonding elements in FIG. 5 are indicated by like reference numerals. Capital letters A-H indicate output terminals of the transmission delay circuit 13, while small letters a-h show input terminals of the distributor 15. The transmission delay circuit 13 is equipped with eight delay elements similar to those depicted in FIG. 3(a). These eight delay elements correspond to eight array elements which form a single ultrasonic beam.

To have the ultrasonic beam form a point of convergence at an optimum position, the delay times of the eight delay elements are set by the microprocessor 12. Upon subsequent energization of transmission delay circuit 13, successively delayed pulses are outputted from the respective output terminals A-H. In this case, the individual output terminals A-H correspond to the eight array elements in the order of arrangement, which array elements are adapted to form an ultrasonic wave. The delay time is the shortest in the case of the output pulses from the terminals A,H and then becomes successively longer in the order of the terminals B,G, the terminals C,F and the terminals D,E.

The matrix circuit 14 is of the same construction as those employed generally. It is constructed of eight input lines from the transmission delay circuit 13, eight output lines crossing with the input lines, and switching elements (not shown) for selectively connecting the crossing input and output lines. 64 (8×8) switching elements are provided. Their switching operation is controlled by the microprocessor 12. Further, the eight output lines are connected to the input terminals a-h of the distributor 15, respectively.

Now assume that by a command from the microprocessor 12, the switching elements indicated by squares in the matrix circuit 14 have been switched into a conductive state and the other switching elements have been brought into a non-conductive state. The output terminals A-H of the transmission delay circuit 13 are successively connected to the input terminals a-h of the distributor 15. As a result, a first combination of delay times is established with the shortest delay time being set for the input terminals a,h and the longest delay time being set for the input terminals d,e. This first combination corresponds to the combination of the array elements $10_1$-$10_8$ which forms the first ultrasonic beam $B_1$.

When the microprocessor 12 brings only the switching elements at triangles into a conductive state, the terminals A-H are successively connected to the terminals b-h,a. Accordingly, a second combination is established with the shortest time set for the terminals b,a and the longest time set for the terminals e,f. This second combination corresponds to the combination of the array elements $10_2$-$10_9$ which forms the ultrasonic beam $B_2$. When the switching elements only at circles are brought into a conductive state, is established a third combination corresponding to the combination of the array elements $10_3$-$10_{10}$ which forms an ultrasonic beam $B_3$. As the switching elements are then successively actuated in a similar manner, up to eight combinations are established over the input terminals a-h. The next, i.e., the ninth combination has the same delay time as the first combination. Such combinations are continually and repeatedly established.

(II) Operation of the Distributor 15

FIG. 7 is a circuit diagram showing the circuit construction of the distributor 15. In the drawing, a-h indicate the same input terminals of the distributor 15 as those depicted in FIG. 6. Further, numerals 1-128 indicate the 1st-128th output terminals of the distributor 15. These output terminals corresponding to the array elements $10_1-10_{128}$, respectively. Delay pulses inputted to the input terminal a are distributed, as shown in the drawing, to the 1st-121th output terminals connected to the input terminal a. Similarly, delay pulses inputted to the input terminals b-h are distributed to the illustrated individual output terminals connected thereto. As will be described subsequently, the 1st-128th output terminals are connected to corresponding trigger circuits which serve to trigger corresponding pulsers in the transmit-receive circuit 16. These trigger circuits are rendered conductive successively 8 circuits by 8 circuits, the eight circuits in each group being brought into a conductive state at the same time, while shifting one circuit by one circuit this conversion of the trigger circuits into the conductive state. Accordingly, only the successive eight output terminals among the entire output terminals effectively output delay trigger signals. Taking the individual input terminals a-h by way of example, only one of the output terminals connected to these input terminals always outputs a delay trigger signal.

When the beam $B_1$ is formed by the array elements $10_1-10_8$ for example, the trigger circuits connected to the 1st-8th output terminals are brought into a conductive state so that pulses of the shortest delay time are outputted from the 1st and 8th output terminals while pulses of the longest delay time are outputted from the 4th and 5th output terminals. When the beam $B_2$ is next formed by the array elements $10_2-10_9$, the trigger circuits connected respectively to the 2nd-9th output terminals are then brought into a conductive state. On the other hand, concurrent with this, the actuation of the matrix circuit 14 depicted in FIG. 6 moves from the switching elements at the positions of the squares to the positions of the triangles, whereby the latter switching elements are brought into a conductive state. Therefore, pulses of the shortest delay time are inputted to the input terminals b,a and pulses of the longest delay times are inputted to the input terminals e,f. As a result, pulses of the shortest delay time are outputted to the 2nd and 9th output terminals while pulses of the longest delay time are outputted to the 5th and 6th output terminals, respectively.

In this manner, conduction of the trigger circuits connected to the respective output terminals is shifted one circuit by one circuit and at the same time, the delay times of the input terminals a-h are also shifted one by one. Accordingly, the eight array elements employed to form an ultrasonic beam are always vibrated with the delay times satisfying the relationship of the inequality (1).

(III) Operations of the Transmit-Receive Circuit 16 and Shift Register 17

FIG. 8 is a circuit diagram around the transmit-receive circuit 16, in which elements identical to the corresponding elements shown in FIG. 5 are identified by like symbols. There are shown AND gates $X_1-X_{128}$, pulsers $P_1-P_{128}$, and receivers $R_1-R_{128}$. One AND gate, one pulser and one receiver are provided for each of the array elements $10_1-10_{128}$. One input terminals of the AND gates $X_1-X_{128}$ are connected to the 1st-128th output terminals of the distributor 15, and the other input terminals are connected to the 1st -128th output terminals of the shift register 17. As described above in the description of the operation of the distributor 15 in (II), the AND gates $X_1-X_{128}$ make up the trigger circuits which trigger the pulsers $P_1-P_{128}$, respectively. The 1st-128th output terminals of the shift register 17 are connected to the AND gates $X_1-X_{128}$ as described above and also to the receivers $R_1-R_{128}$. On the other hand, the output terminals of the receivers $R_1-R_{128}$ are connected to the corresponding 1st -128th input terminals of the adder 18.

In accordance with a command from the microprocessor 12, the shift register 17 simultaneously outputs pulses from eight consecutive output terminals and shifts the output of pulses one terminal by one terminal. Now assume that the ultrasonic beam $B_1$ is to be formed by the array elements $10_1-10_8$. Pulses are outputted from the 1st-8th output terminals of the shift register 17, whereby one input terminals of the AND gates $X_1-X_8$ are changed to a high level. At the same time, the receivers $R_1-R_8$ are triggered so that these receivers are brought into an activated state. At this time, pulses delayed by prescribed times as described above are outputted from the 1st-8th output terminals of the distributor 15. The other input terminals of the AND gates $X_1-X_8$ take a high level after the pulse delay times for the 1st-8th terminals of the distributor 15. At this time point, the AND gates are brought into a conductive state so that trigger signals adapted to trigger the corresponding pulsers are outputted. As already mentioned above in the description of the distributor 15, the outputs from the first and eighth output terminals take place first and the output from the fifth output terminal occurs last. The outputs of pulses form the pulsers $P_1-P_8$ also occur correspondingly. As a consequence, the array elements $10_1,10_8$ are vibrated first and the array elements $10_4,10_5$ are vibrated last, so that the desired ultrasonic wave B1 is formed.

Upon radiation of the ultrasonic beam $B_1$ against the specimen, reflected waves enter the individual array elements $10_1-10_8$ so that they are converted to corresponding electrical signals. Signals of reflected waves outputted from the respective array elements $10_1-10_8$ in the above manner are separately amplified by the receivers $R_1-R_8$ and then inputted to the 1st-8th input terminals of the adder 18, respectively. In this case, needless to say, among the reflected waves entering the respective array elements $10_1-10_8$, the entering of the reflected waves in to the array elements $10_1,10_8$ take place first while that of the reflected waves into the array elements $10_4,10_5$ occur last. Accordingly, the signals of reflected waves to be inputted to the 1st and 8th input terminals of the adder 18 are outputted first while the reflected wave signals to be inputted to the 4th and 5th input terminals are outputted last.

Subsequent to the formation of the ultrasonic beam $B_1$, the outputs from the shift register 17 are shifted by one output terminal so that pulses are outputted from the eight output terminals numbered from the 2nd to the 9th. Further, the delay pattern of delay pulses which appear at the output terminals of the distributor 15 is also shifted by one output terminal. Namely, delay pulses are outputted with the shortest delay time from the 2nd and 9th output terminals while delay pulses are outputted with the longest delay time from the 4th and 5th output terminals. As a result, the array elements $10_2$–$10_9$ are vibrated with the corresponding delay times so that the desired ultrasonic beam $B_2$ is formed. Signals of resulting reflected waves are amplified by the corresponding receivers $R_2$–$R_9$ and are then inputted to the 2nd–9th input terminals of the adder 18 with time intervals corresponding the delay times. In a similar manner, reflected wave signals are then successively inputted to the input terminals of the adder 18.

(IV) Operations of the Adder 18, Matrix Circuit 19 and Waveform Adder 20

As illustrated in FIG. 8, the adder 18 is provided with 1st–128th input terminals which are connected to the receivers $R_1$–$R_{128}$, respectively. Incidentally, the adder 18 has the same circuit construction as the distributor 15 except that the input-output relationship is opposite. Therefore, the 1st–128th terminals in FIG. 7 correspond to the input terminals of the adder 18 and the terminals a–h correspond to output terminals of the adder 18. As is apparent from the foregoing, it is only the consecutive eight receivers that reflected wave signals are inputted. Of the 128 input terminals of the adder 18, it is only the consecutive eight input terminals that reflected wave signals are inputted. A signal of reflected wave is therefore inputted to only one of the input terminals which are associated with the output terminals a–h.

A description will next be made using the preceding example. When the ultrasonic beam $B_1$ is radiated, reflected wave signals are inputted to the 1st–8th input terminals of the adder 18 and these signals are then outputted, as they are, from the output terminals a–h. When the ultrasonic beam $B_2$ is radiated on the other hand, reflected wave signals are inputted to the 2nd–9th input terminals of the adder 18 and are then outputted, as they are, from the output terminals a–h.

The matrix circuit 19 has the same circuit construction as that shown in FIG. 6 except that the output terminals and input terminals are opposite. Namely, the input terminals of the matrix circuit 19 correspond to the terminals a–h shown in FIG. 6. These input terminals a–h are connected to the corresponding ones of the output terminals a–h of the adder 18. The manner of switching of the individual switching elements of the matrix circuit 19 are the same as the manner of switching of the matrix circuit 14. Assume that signals of reflected waves of the ultrasonic beam $B_1$ are inputted to the input terminals a–h. Among the switching elements of the matrix circuit 19, those located at the points of squares shown in FIG. 6 are switched into a conductive state. These signals of reflected waves are therefore outputted from the corresponding output terminals A–H. Similarly, when signals of reflected waves of the ultrasonic beam $B_2$ are inputted to the input terminals a–h, the switching elements at the points of triangles are brought into a conductive state so that the signals of reflected waves at the input terminals a–h are outputted from the output terminals H,A–G, respectively.

Regarding the ultrasonic beams $B_1$, $B_2$ and $B_3$, the relationship among the signals of their reflected waves at the input terminals in the adder 18 and at the input terminals and output terminals in the matrix circuit 19 can be illustrated as shown in the following table.

| Ultrasonic beam | $B_1$ | $B_2$ | $B_3$ |
| --- | --- | --- | --- |
| Input terminals of adder 18 | 1–8 | 2–9 | 3–10 |
| Input terminals of matrix circuit 19 | a–h | b–a | c–b |
| Output terminals of matrix circuit 19 | A–H | A–H | A–H |

As is apparent from the above table, the reflected wave signals from the vibrated consecutive eight array elements are always outputted from the output terminals A–H of the matrix circuit 19 in the order of arrangement of the array elements no manner how these array elements are selected.

The reflected wave signals outputted from the output terminals A–H are inputted to the waveform adders 20, respectively. The waveform adders 20 are equipped with delay circuits, which are connected respectively to the above output terminals, and also with an addition circuit for adding reflected wave signals outputted from these delay circuits, although neither the delay circuits nor the addition circuit is shown in the drawing. The respective delay circuits are provided to bring the phases of reflected wave signals, said phases being different from one another, into coincidence and add the individual reflected wave signals in the same phase at the above addition circuit. In accordance with the inequality (1), reflected wave signals are outputted last from both the end elements of the eight array elements and reflected wave signals are outputted first from the central array elements. Therefore, the delay time of the delay circuits connected to the output terminals A,H of the matrix circuit 19 are the shortest and the delay time of the delay circuits connected to the output terminals D,E is the longest. When suitable delay times are set for the individual delay circuits in the manner described above, the phases of reflected wave signals outputted from these delay circuits are coincided so that these reflected wave signals are added in the same phase at the addition circuit.

The operation of the control circuit 11 has been described above. Outputs from this control circuit 11 are signals of reflected waves of the individual ultrasonic beams. Based on the reflected wave signals, the existence or non-existence of one or more defects in a specimen is determined. A description will hereinafter be made of one example of processing suitable for the above determination.

Each signal of reflected wave obtained at the control circuit 11 is inputted to a peak detector to detect its peak value. After the peak value so detected is then converted to a digital value by an A/D converter, the digital value is inputted to an image processor. At the image processor, it is judged whether the peak value is greater than a preset threshold or not. To a display, the image processor outputs, for example, a low-level signal when the peak value is greater than the threshold and a high-level signal when the peak value is not greater than the threshold. As a result, the display gives, for example, a black-level display when no defect is present or a white-level display when a defect is present. Since similar processing is performed for each beam, the existence or non-existence of a defect in an entire planar cross-section at a given depth of a specimen is clearly displayed as a plan by electronic scanning with the ultrasonic beams $B_1$–$B_{121}$ from the array probe 10 in the direction of X-axis and by mechanical scanning in which the array probe 10 is moved in the direction of Y-axis.

The above-described conventional ultrasonic flaw detector can inspect with extreme certainty the existence or non-existence of a defect in a specimen. There is a strong desire for a still faster inspection speed where many specimens are inspected by the above ultrasonic flaw detector. The inspection speed of the ultrasonic flaw detector is however governed by the time required for one electronic scanning operation, namely, by (the number of ultrasonic beams) x (switching speed). Here, the switching speed is usually set equal to the repetition speed (frequency) of the pulsers which are adapted to vibrate array elements. It is therefore difficult to shorten the above time, resulting in the problem that as the area of a specimen to be inspected in the direction of X-axis (the direction of electronic scanning) becomes greater, more ultrasonic beams are required and naturally a longer inspection time is needed.

An object of the present invention is therefore to overcome the above-described problem of the prior art and to provide an ultrasonic flaw detector capable of substantially shortening the electronic scanning time, in other words, the inspection time for a specimen.

SUMMARY OF THE INVENTION

To achieve the above object, the present inventors firstly contemplated of dividing array elements into blocks of plural array elements and providing each block with a control unit similar to those employed in the conventional detector. This approach however developed another problem that ultrasonic beams were unavoidably omitted between the adjacent blocks since plural array elements were used for the formation of each ultrasonic beam. The present inventors have then proceeded with a further investigation, resulting in the invention of a means for substantially shortening the electronic scanning time without such omission of ultrasonic beams. Namely, the present invention provides an ultrasonic flaw detector having an array probe formed of a number of array elements arranged in a line, pulsers for feeding delay pulses to plural ones of the array elements to vibrate the plural array elements, and receivers for receiving signals of reflected wave of an ultrasonic beam by the plural array elements, vibration of said array elements being successively shifted to conduct scanning by ultrasonic beams, characterised in that the entire array elements are divided into plural blocks with groups of some of said array elements overlapping between adjacent ones of the plural blocks, and each of the blocks is provided with a block selecting means for selecting plural ones of the array elements in the same block and shifting vibration of the array elements in the same block, an input/output unit for receiving signals from individual receivers for the same block and outputting the thus-inputted signals, and a switching means for causing the array elements in each of the groups to belong first to one of the same block and an adjacent one of the blocks and then to the other block.

In the above construction, the many array elements arranged in a line are divided into the plural blocks. The pulsers and receivers, which are connected to these array elements, are also divided into the same blocks. When delay pulses are outputted from plural ones of the pulsers in each block thus divided, the array elements connected to these pulsers are vibrated to radiate an ultrasonic beam. These array elements then receive its reflected waves and output reflected wave signals. These reflected wave signals are fed through the receivers connected to the vibrated array elements, inputted to the corresponding input/output terminals of the input/output unit, and then outputted together. In the invention, the array elements in each overlapped group is caused by a switching means to belong first to one of the associated blocks and then to the other block. This switching has made it possible to avoid omission of ultrasonic beams between blocks.

Vibration of plural array elements in each block is shifted one element by one element. As a result, electronic scanning with ultrasonic beams can be performed in each block. Reflected wave signals as many as the blocks are hence collected at the same time per line, leading to a substantial reduction in the electronic scanning time.

BRIEF DESCRIPTION OF THE DRAWINGS

FIG. 12 shows various data;

FIGS. 14(a), 14(b), 14(c) and 14(d) are circuit diagrams of a matrix circuit.

DETAILED DESCRIPTION OF THE PREFERRED EMBODIMENTS

To describe the present invention in more detail, the invention will now be described with reference to the accompanying drawings.

Figure 9:
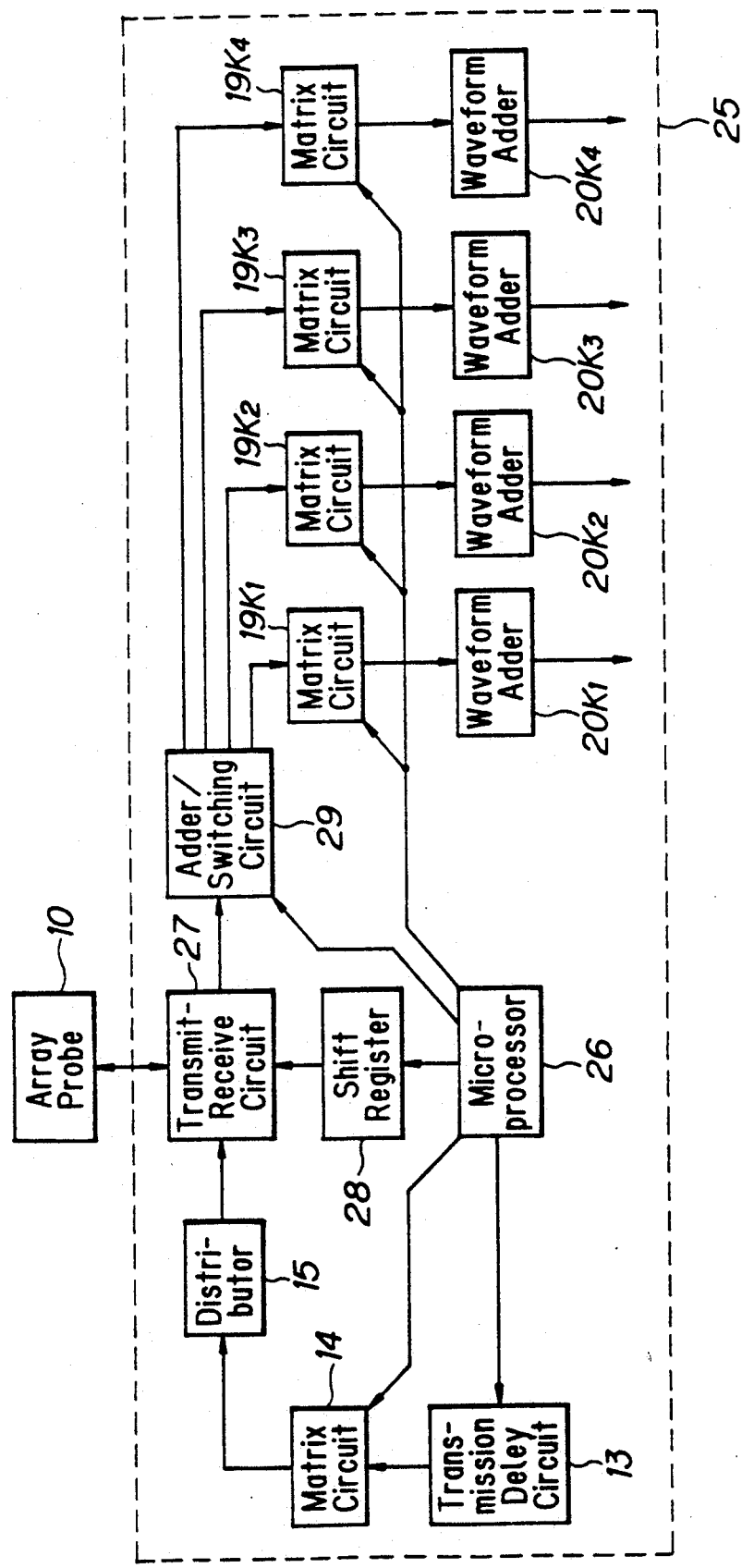
FIG. 9 a block diagram of a control unit of an ultrasonic flaw detector according to one embodiment of the present invention.
Figure 10:
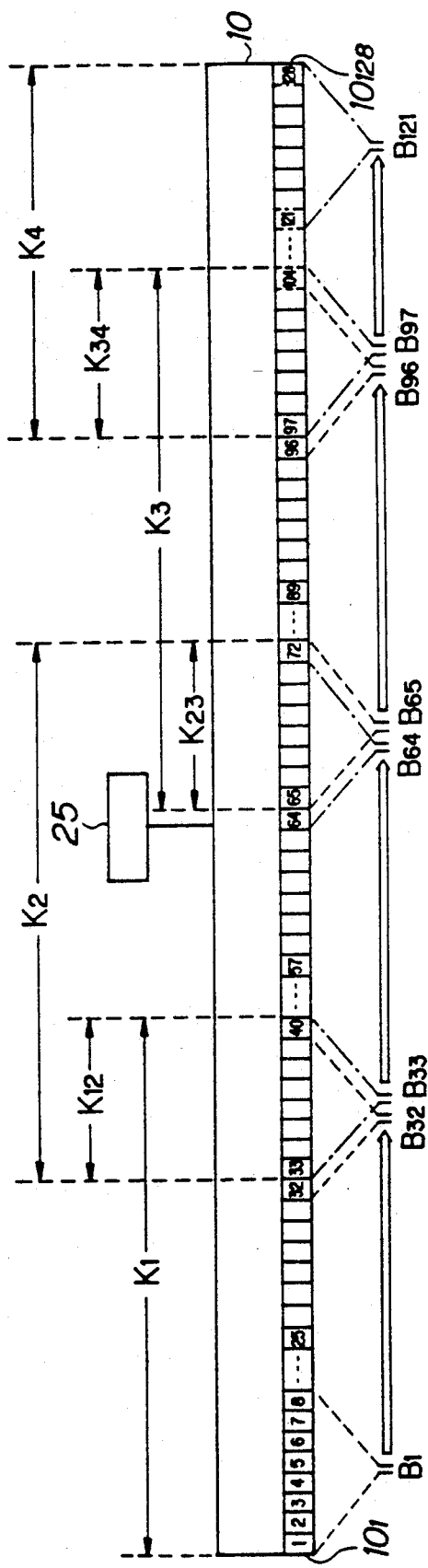
FIG. 10 illustrates the arrangement of array elements.

FIG. 9 is a block diagram of an ultrasonic flaw detector according to one embodiment of the present invention, and FIG. 10 shows the arrangement of array elements and illustrates the concept of a method for vibrating the array elements in the embodiment depicted in FIG. 9. In this embodiment, similarly to the examples described above, a description will be made assuming that the number of the array elements, the pitch of the array elements, the number of array elements vibrated at the same time, and the number of ultrasonic beams are 128, 1 mm, 8 and 121.

First of all, the concept of the vibration method in this embodiment is described with reference to FIG. 10. FIG. 10 shows an array probe 10 and array elements $10_1$–$10_{128}$, which are the same as the conventional ones. Designated at numeral 25 is a control circuit in the present embodiment. Its construction is illustrated in FIG. 9. In this embodiment, upon vibration of the array elements, the 128 array elements are divided into 4 blocks $K_1$, $K_2$, $K_3$ and $K_4$. Symbols $K_{12}$, $K_{23}$ and $K_{34}$ indicate boundary sections where the blocks are overlapped. Namely, the individual blocks $K_1$–$K_4$ are set with some of the array elements being shared. Further, the array elements in each of these boundary sections $K_{12}, K_{23}, K_{34}$ are vibrated by causing them to belong to one of the adjacent blocks during a prescribed time period in each electronic scanning period and to the other block during another time period.

Described more specifically, the blocks $K_1$, $K_2$, $K_3$ and $K_4$ are constructed of array elements $10_1$–$10_{40}$, array elements $10_{33}$–$10_{72}$, array elements $10_{65}$–$10_{104}$ and array elements $10_{97}$–$10_{128}$, respectively. On the other hand the boundary sections $K_{12}$, $K_{23}$ and $K_{34}$ are constructed, of array elements $10_{33}$–$10_{40}$, array elements $10_{65}$–$10_{72}$ and array elements $10_{97}$–$10_{104}$. Upon electronic scanning, the boundary sections $K_{12}, K_{23}, K_{34}$ are first caused to belong to the blocks $K_2$, $K_3$ and $K_4$ to take part in the formation of ultrasonic beams. Thereafter, they are caused to belong to the blocks $K_1$, $K_2$, and $K_3$ to take part in the formation of ultrasonic beams. Namely, the electronic scanning are first initiated simultaneously by a beam $B_1$ from the block $K_1$, a beam $B_{33}$ from the boundary section $K_{12}$ caused to belong to the block $K_2$, a beam $B_{65}$ from the boundary section $K_{23}$ caused to belong to the block $K_3$ and a beam $B_{97}$ from the boundary section $K_{34}$ caused to belong to the block $K_4$.

When the electronic scanning advances in a direction indicated by arrows in FIG. 10 and the use of the array elements in the boundary sections $K_{12}, K_{23}, K_{34}$ for the formation of the ultrasonic beams is completed, the boundary sections $K_{12}, K_{23}, K_{34}$ are then caused to belong to the blocks $K_1, K_2, K_3$ respectively at a suitable time. The array elements in these boundary sections then take part along with the array elements in the blocks, to which the boundary sections belong, in the formation of ultrasonic beams for the continuation of the electronic scanning. Eventually, the electronic scanning is completed by the radiation of an ultrasonic beam $B_{32}$ formed by the eight array elements ranging from the array element $10_{32}$ in the block $K_1$ to the array element $10_{39}$ in the boundary section $K_{12}$, an ultrasonic beam $B_{64}$ formed by the eight array elements ranging from the array element $10_{64}$ in the same block $K_2$ to the array element $10_{71}$ in the boundary section $K_{23}$, an ultrasonic beam $B_{96}$ formed by the eight array elements ranging from the array element $10_{96}$ in the block $K_3$ to the array element $10_{103}$ in the boundary section $K_{34}$, and an ultrasonic beam $B_{121}$ formed by the eight array elements ranging from the array element $10_{121}$ to the array element $10_{128}$ in the block $K_4$. It is therefore possible to obviate the omission of ultrasonic beams, which takes place between the adjacent blocks when the array probe is divided simply into 4 blocks. A description will hereinafter be made of a construction for conducting such electronic scanning.

Figure 1:
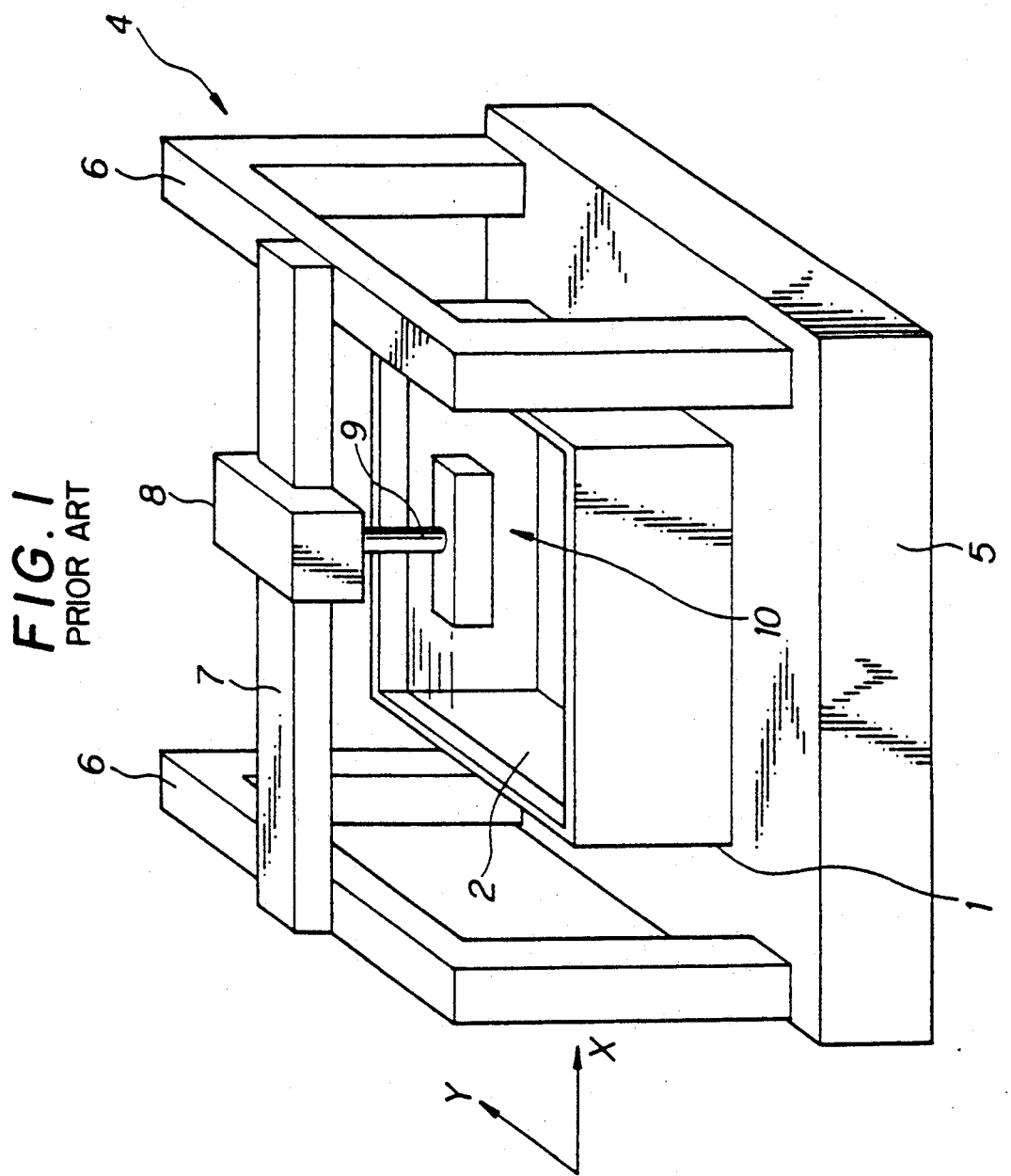
FIG. 1 is a perspective view of a scanner unit of a conventional ultrasonic flaw detector.
Figure 2A:
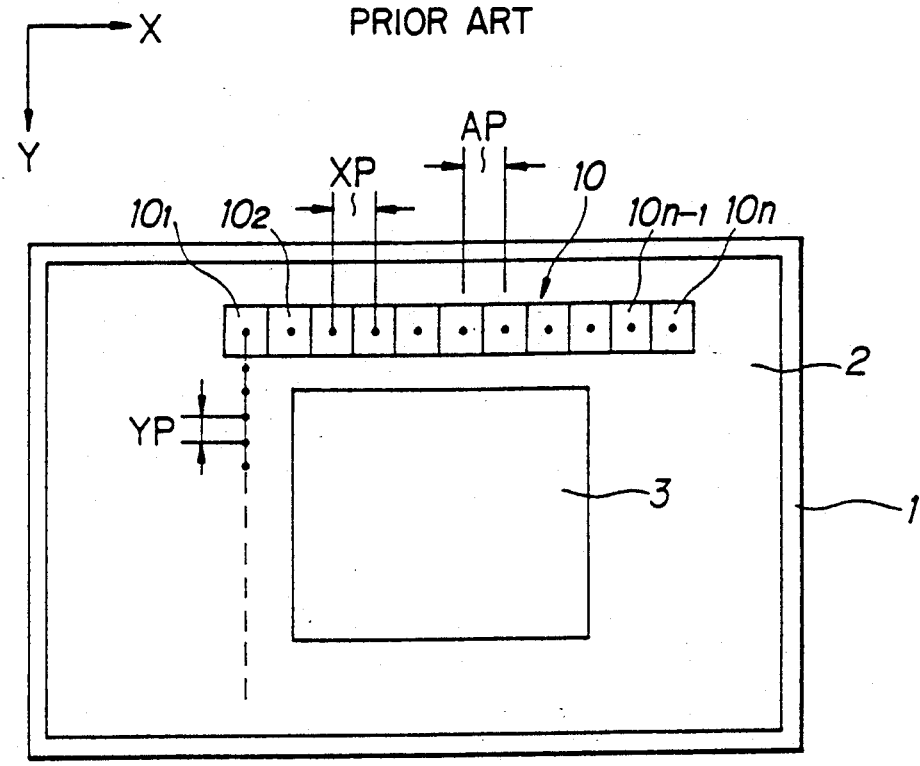
FIGS. 2(a) and 2(b) are plan and side views of an array probe.
Figure 2B:
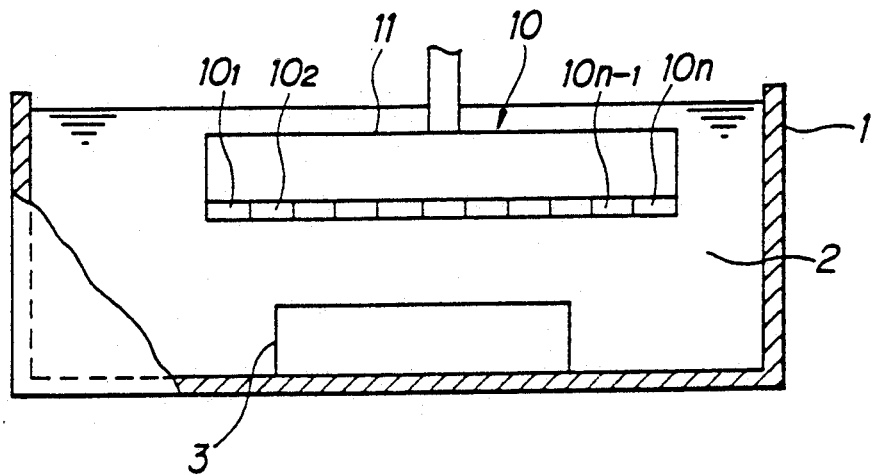
Figure 3B:
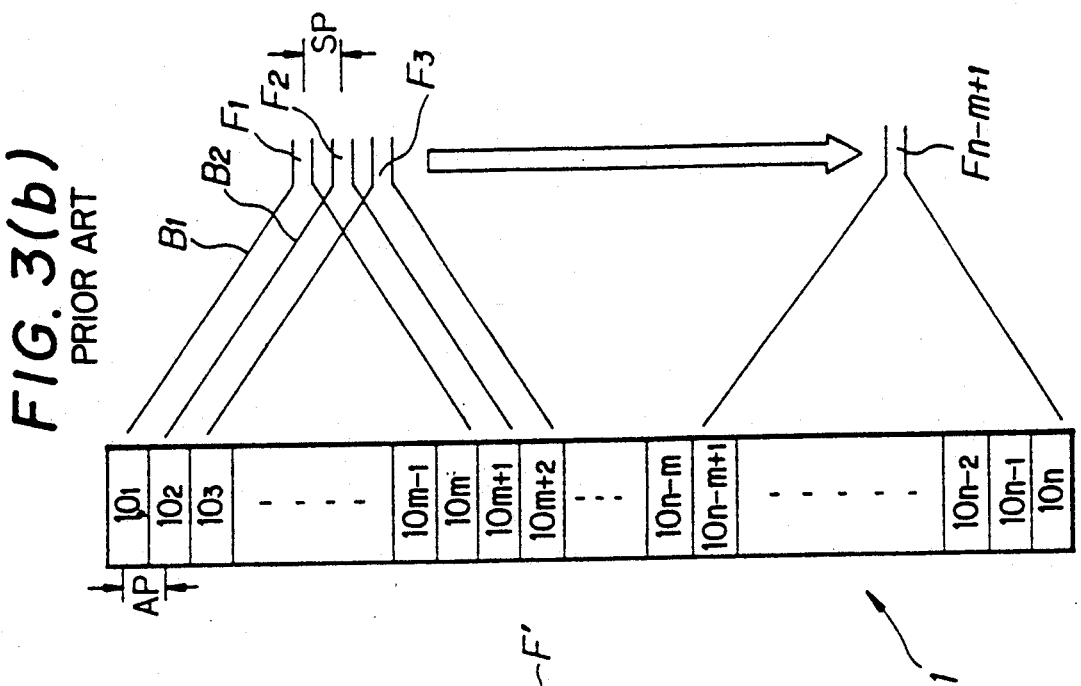
FIGS. 3(a) and 3(b) are schematic illustrations showing the function of the array probe.
Figure 3A:
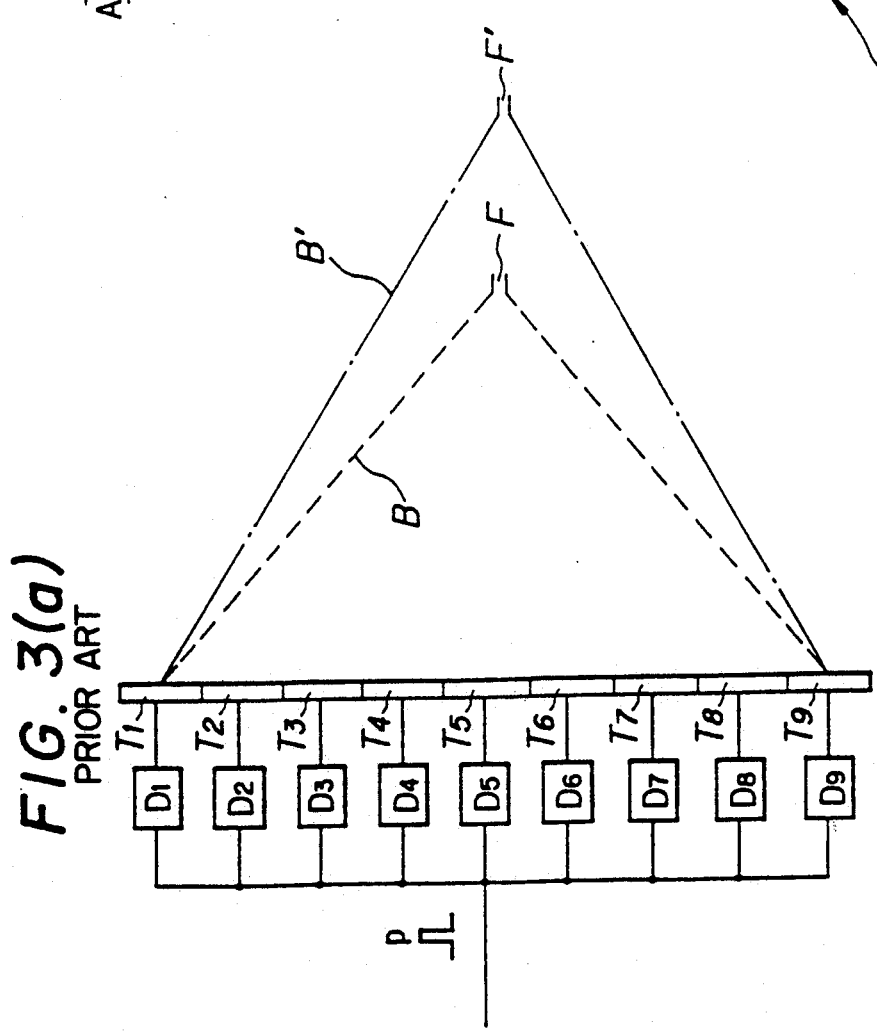
Figure 4:
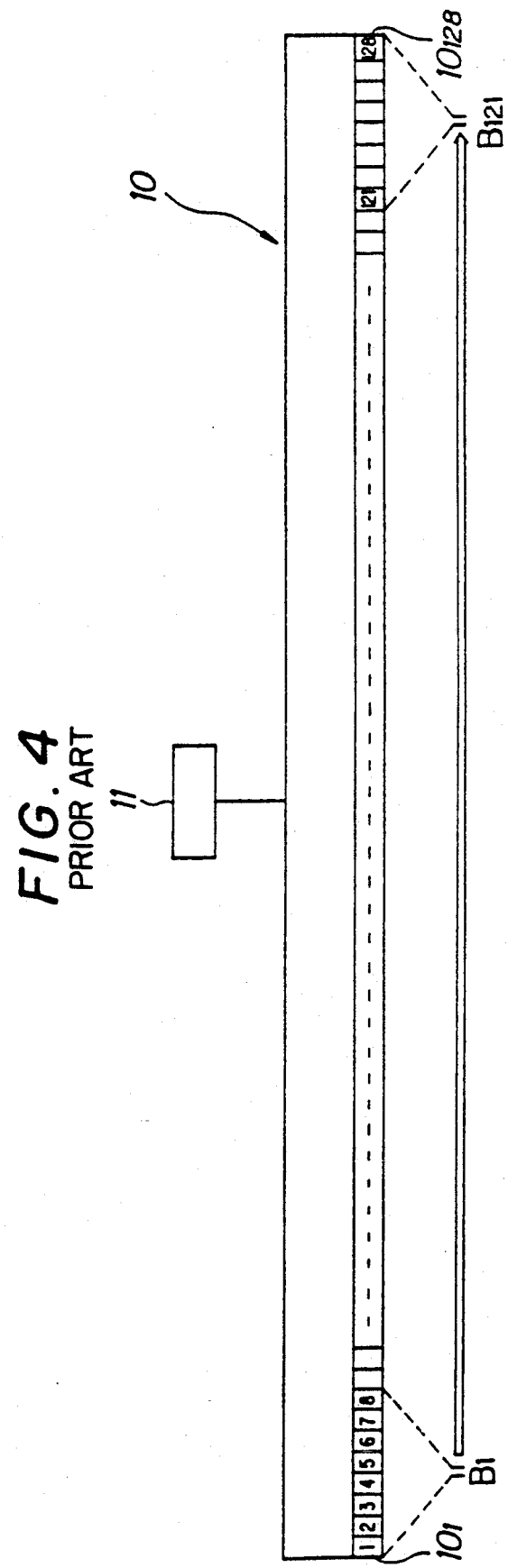
FIG. 4 shows the arrangement of array elements.
Figure 5:
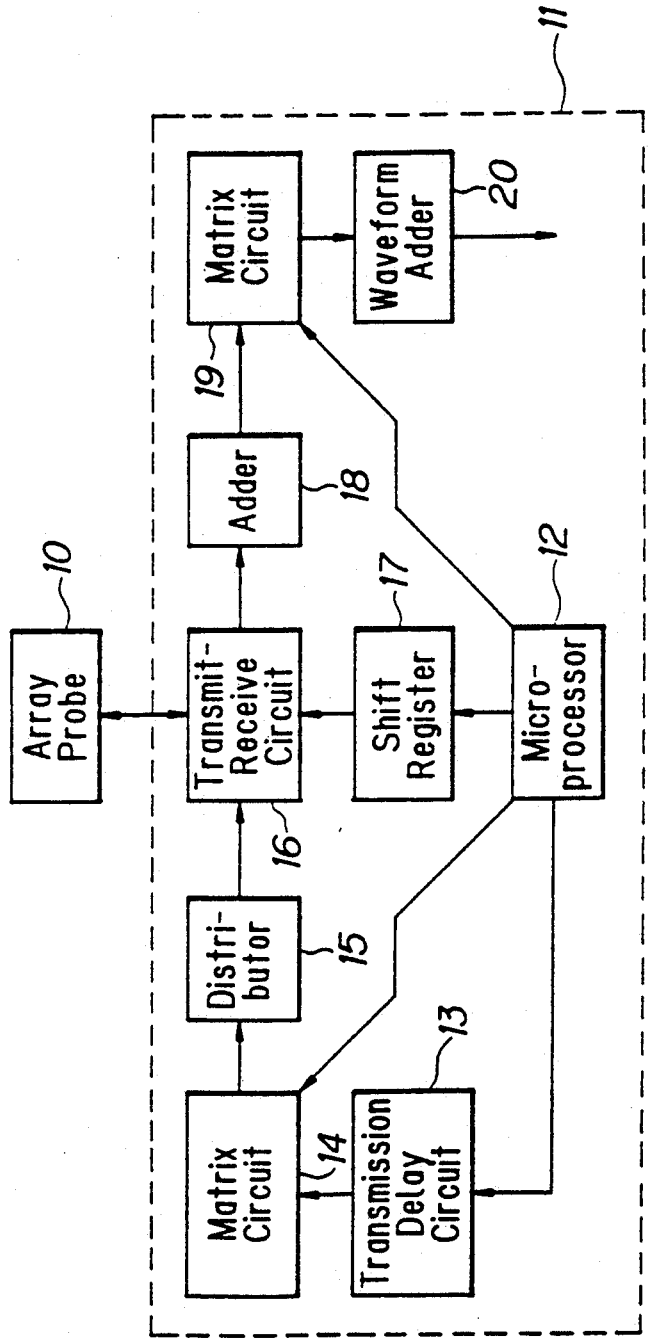
FIG. 5 is a block diagram of a control unit shown in FIG. 4.
Figure 6:
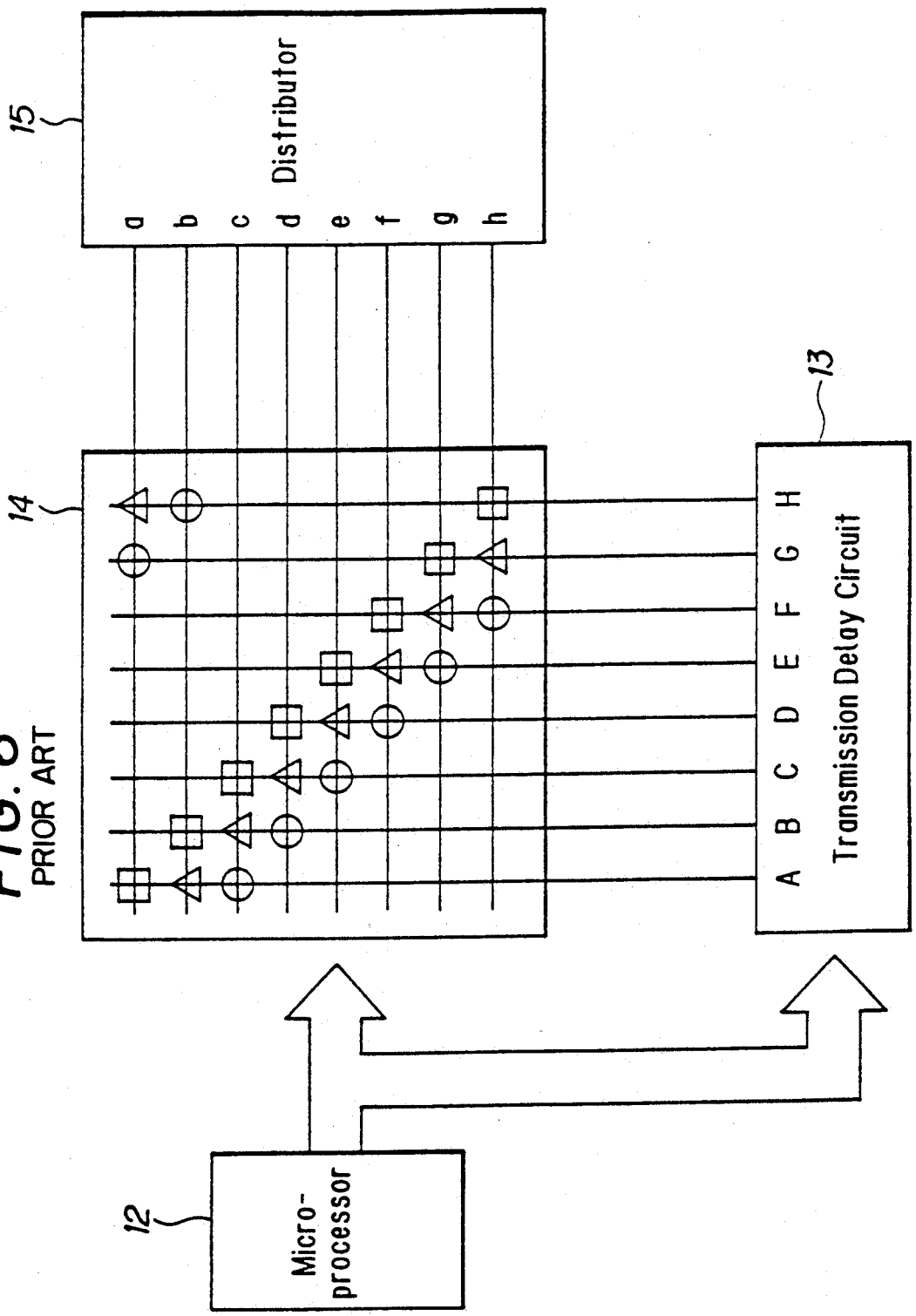
FIGS. 6, 7 and 8 are circuit diagrams of a matrix circuit, distributor and transmit-receive circuit depicted in FIG. 5.

In the block diagram shown in FIG. 9, the same elements of structure as the corresponding elements depicted in FIG. 5 are indicated by like symbols and their description is omitted herein. Numeral 25 indicates the control circuit in this embodiment. There are also shown a microprocessor 26, a transmit-receive circuit 27, and a shift register 28. They have substantially the same constructions as the microprocessor 12, transmit-receive circuit 16 and shift register 17 except that the array probe 10 is operated as the above-described blocks. Further, the microprocessor 26 is different in that it performs control of switching elements, which will be described subsequently herein, in addition to the control of the blocks. Designated at numeral 29 is an adder/switching circuit, whose construction will also be described subsequently herein. There are also shown matrix circuits $19K_1$–$19K_4$ and waveform adders $20K_1$–$20K_4$. They have the same functions as the matrix circuit 19 and waveform adder 20 depicted in FIG. 5.

Figure 11A:
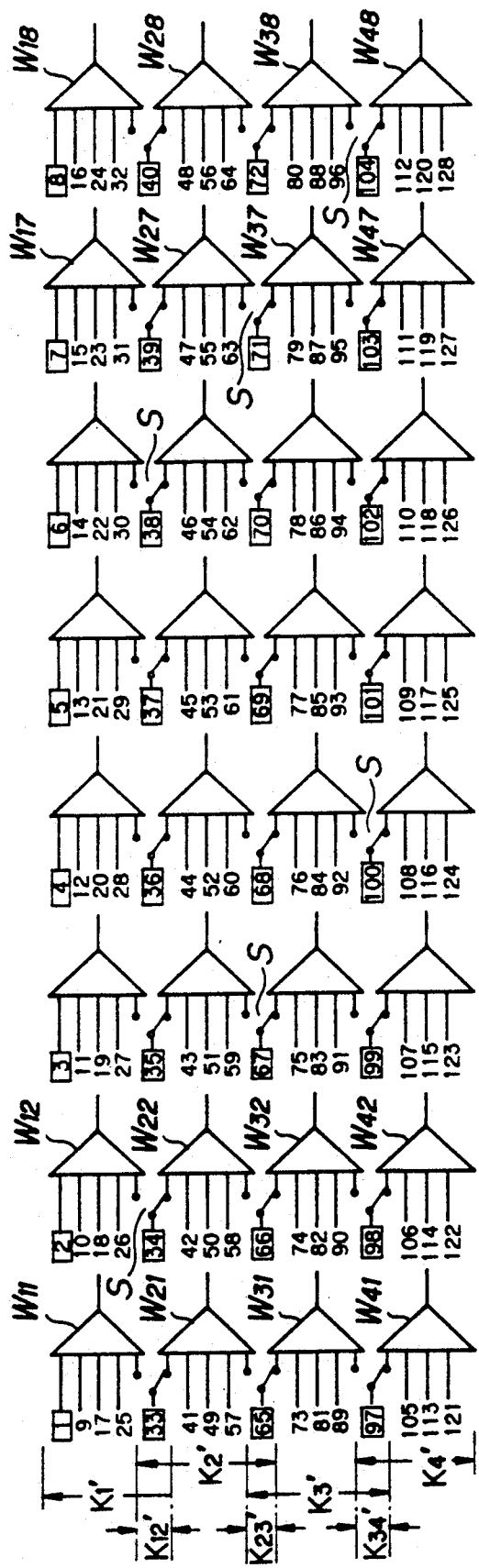
FIGS. 11(a), 11(b), 11(c) and 11(d) are circuit diagrams of an adder/switching circuit shown in FIG. 9.
Figure 11B:
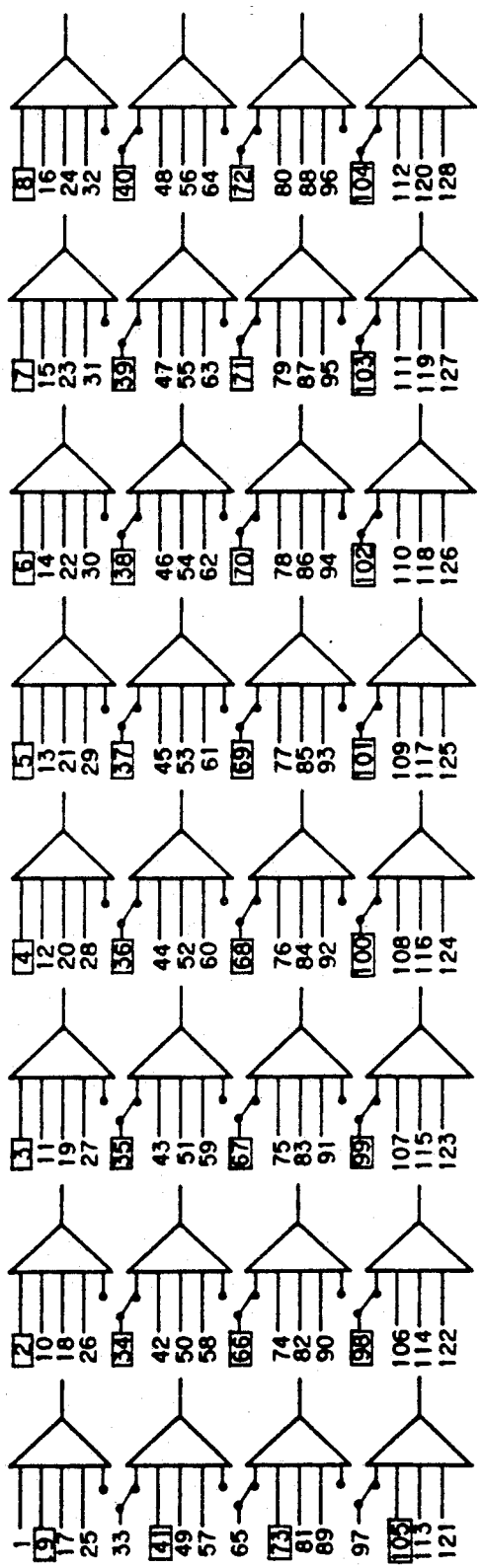

FIG. 11(a) is a circuit diagram of the adder/switching circuit shown in FIG. 9. In the drawing, there are shown input terminals 1–128 of the adder/switching circuit 29, adders $W_{11}$–$W_{48}$, and switches S. Corresponding to the array probe 10, the adder/switching circuit 29 is also divided into blocks $K_{1'}$–$K_{4'}$ and intermediate sections $K_{12'}, K_{23'}, K_{34'}$ as shown in the drawing. Namely, the block $K_{1'}$ comprises the adders $W_{11}$–$W_{18}$. The 1st–32th input terminals are connected to the adders $W_{11}$–$W_{18}$ in the arrangement illustrated in the drawing. Further, to the individual adders $W_{11}$–$W_{18}$, ones of switching terminals of the respective switches S are connected along with the corresponding input terminals. The remaining blocks $K_{2'}$–$K_{4'}$ also have a similar construction. On the other hand, the intermediate section $K_{12'}$, comprises the 33rd–40th input terminals, which are connected to the corresponding switches S. The remaining intermediate sections $K_{23'}, K_{34'}$ have a similar construction. All the switches S are arranged in such a way that they can be switched over in an interlocked manner by a command from the microprocessor 26. By this switching, a selection is made regarding the blocks to which the input terminals making up the respective intermediate sections are caused to belong as input terminals of the corresponding adders.

Incidentally, no more than one signal is simultaneously inputted through the individual input terminals of each adder, as will be described subsequently. Since signals inputted to the remaining input terminals are all zero, each adder is merely a connector means that outputs a signal which has been inputted through anyone of the input terminals as is.

Next, the operation of this embodiment will be described with reference to the circuit diagrams of the adder/switching circuit 29, which circuit diagrams are illustrated in FIGS. 11(a)–11(d). First, the switches S of the adder/switch circuit 29 are switched to their respective positions shown in FIG. 11(a). The intermediate sections $K_{12'}, K_{23'}, K_{34'}$ are therefore caused to belong to the blocks $K_{2'}, K_{3'}, K_{4'}$, respectively. The operation is the same as that of the conventional detector until delay pulses are outputted from the distributor 15. In this embodiment, in accordance with commands from the microprocessor 26, signals are outputted from the 1st–8th output terminals, 33rd–40th output terminals, 65th–72nd output terminals and 97th–104th output terminals, respectively. Thereafter, the output from the output terminals of the shift register 28 is shifted one terminal by one terminal successively. Namely, the output terminals of the shift register 28 are divided into four blocks which consist of the 1st–40th output terminals, the 33rd–72nd output terminals, the 65th–104th output terminals and the 97th–128th output terminals, respectively. In each block, signals are simultaneously outputted from eight output terminals. The output from the output terminals is shifted. The division of the array elements into blocks by the shift register 28 is not changed once the direction of electronic scanning is determined. It is here that this division is different from the division into the blocks upon vibration, the latter division being shown in FIG. 10. By signals from the 1st–8th, 33rd–40th, 65th–72nd and 97th–104th output terminals, the shift register 28 triggers the corresponding pulsers of the transmit-receive circuit 27 so that the corresponding array elements are vibrated. In addition, the corresponding receivers are actuated. The four ultrasonic beams $B_1, B_{33}, B_{65}, B_{97}$ are then radiated from the array probe 10. Reflected waves of the these ultrasonic beams $B_1, B_{33}, B_{65}, B_{97}$ enter the vibrated array elements and are inputted as signals of reflected waves to the actuated receivers.

Reflected wave signals outputted from the receivers are inputted to the adder/switching circuit 29. In this case, the input terminals of the adder/switching circuit 29, to which the reflected wave signals are inputted, correspond to the vibrated array elements and actuated receivers. These input terminals are indicated by surrounding them in squares in FIG. 11(a). The reflected wave signals, which have been inputted to these input terminals, are outputted as signals of the corresponding adders because there are no inputs to the other input terminals of these adders. Namely, the input signals to the 1st-8th input terminals are outputted as they are from the adders $W_{11}-W_{18}$, the input signals to the 33rd-40th input terminals from the adders $W_{21}-W_{28}$, the input signals to the 65th-72nd input terminals from the adders $W_{31}-W_{38}$, and the input signals to the 97th-104th input terminals from the adders $W_{41}-W_{48}$.

The output signals from the adders $W_{11}-W_{18}$, namely, the eight output signals from the block $K_{1'}$ are inputted via the matrix circuit $19K_1$ to the waveform adder $20K_1$. After the phases of the eight reflected wave signals brought into coincidence by unillustrated delay circuits respectively, these reflected wave signals are added by the corresponding adder. This operation is the same as the operation of the matrix circuit 19 and waveform adder 20 in the conventional detector. The eight reflected wave signals outputted from each of the blocks $K_{2'}-K_{4'}$ are likewise processed by the matrix circuits $19K_2-19K_4$ and waveform adders $20K_2-20K_4$. As a result, the existence or non-existence of a defect at four points of the specimen based on the signals of reflected waves of the ultrasonic beams $B_1, B_{33}, B_{65}, B_{97}$ are displayed at the same time, for example, on a display of an image processor.

The output of signals from the output terminals of the shift register 28 is next shifted by one output terminal, so that signals are outputted from the 2nd-9th, 34th-41st, 66th-73rd and 98th-105th output terminals. Ultrasonic beams $B_2, B_{34}, B_{66}, B_{98}$ are then radiated from the array probe 10. Signals of reflected waves of these ultrasonic beams are inputted to input terminals of the adder/switching circuit 29, which input terminals are surrounded by squares. Subsequent processing is the same as the processing of the signals of reflected waves of the ultrasonic beams $B_1-B_{97}$. As a result, ultrasonic images of next points of the specimen, said points being shifted by one pitch from the above four points, are displayed.

In this manner, the electronic scanning with ultrasonic beams advances successively in the direction indicated by the arrows in FIG. 10. Upon completion of the scanning with up to the ultrasonic beams $B_8, B_{40}, B_{72}, B_{104}$, the individual switches S of the adder/switching circuit 29 are all changed over to the opposite sides in accordance with commands from the microprocessor 26. As a consequence, the respective array elements of the intermediate sections $K_{12'}, K_{23'}, K_{34'}$ shown in FIG. 11(a) are caused to belong to the blocks $K_{1'}, K_{2'}, K_{3'}$, respectively. The electronic scanning is continuously performed even during this switching.

Figure 11C:
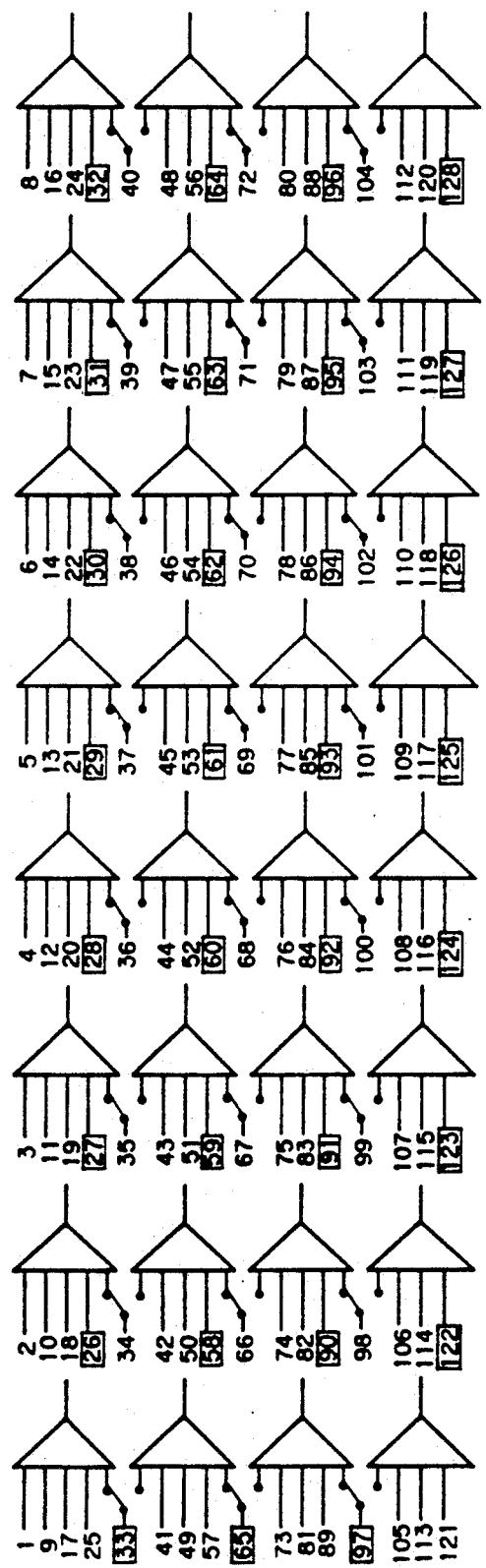
Figure 11D:
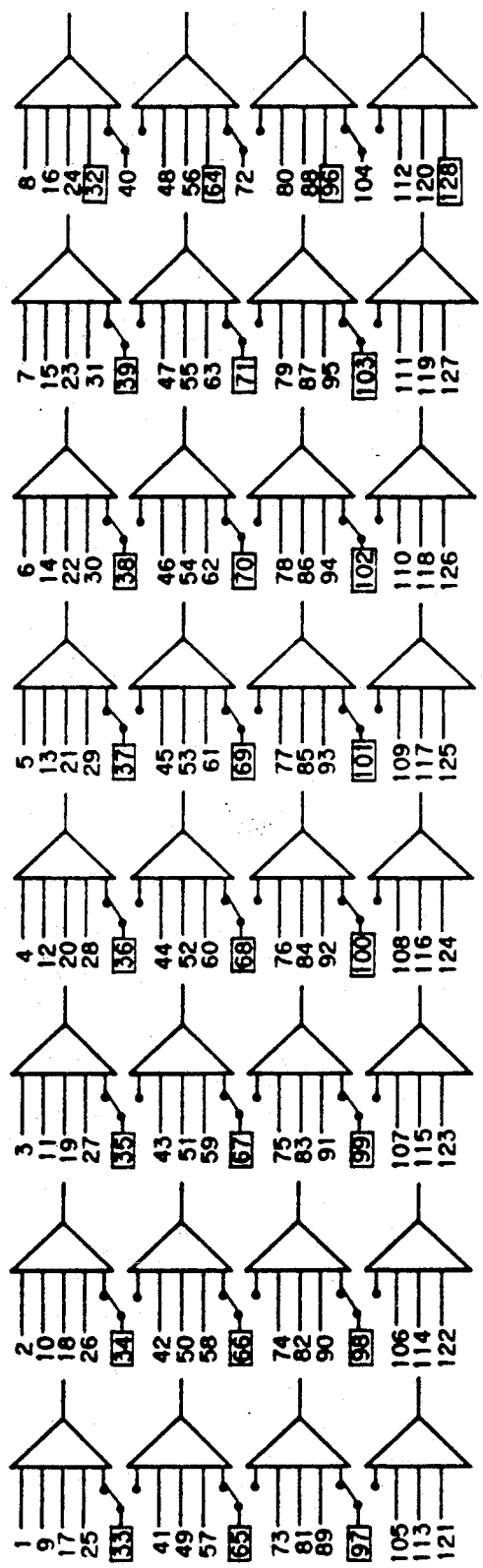

When the electronic scanning proceeds to the ultrasonic beams $B_{26}, B_{58}, B_{90}$ (the scanning in the block $K_{4'}$ has been completed with the ultrasonic beam $B_{121}$ in the previous stage), signals of reflected waves of these ultrasonic beams are inputted to input terminals of the adder/switching circuit 29, said input terminals being surrounded by squares, as shown in FIG. 11(c). In this case, the 33rd, 65th and 97th input terminals of the intermediate sections $K_{12'}, K_{23'}, K_{34'}$ again take part in the input of reflected wave signals. Thereafter, similar processing is performed. The electronic scanning which is continued in the above manner is completed upon radiation of the ultrasonic beams $B_{32}, B_{64}, B_{96}$. Here, these reflected wave signals are inputted to input terminals of the adder/switching circuit 29, said input terminals being surrounded by squares, as shown in FIG. 15(d). Thereafter, similar processing to the aforementioned processing is performed. As a result, the electronic scanning of one line is completed.

In this embodiment, the array elements are divided into the four blocks by the shift register. In each of the blocks, eight consecutive array elements are vibrated while successively shifting the vibration of the array elements one element by element, whereby ultrasonic beams are moved. On the other hand, the input terminals of the adder/switching circuit, to which signals of reflected waves of the ultrasonic beams are inputted, are divided into the four blocks and three intermediate sections. The switches are connected to the input terminals in the intermediate sections, so that the individual input terminals of these intermediate sections can be selectively connected to both of the associated adjacent blocks. It is therefore possible to shorten the speed of electronic scanning to one fourth compared to a conventional flaw detector having the same number of array elements and thus to substantially shorten the inspection time without omission of ultrasonic beams at the boundaries of the four blocks of the array elements. Furthermore, in spite of the division of the array elements into the four blocks, no modification is needed to the matrix circuit which is adapted to apply predetermined delays to the respective pulsers. Although twenty-four switches are provided in the adder/switching circuit, all the switches are changed over at the same time so that the load to the microprocessor is extremely small.

It is to be noted that the number of divisions of the array probe (the number of simultaneous beams), the total number of array elements and the number of array elements taking part in the formation of an ultrasonic beam (the number of simultaneously vibrated elements) can be chosen as desired. These numbers and various numbers based thereon are shown in FIG. 12.

Another embodiment of the present invention will next be described. This embodiment is different from the preceding embodiment only in the constructions of the adder/switching circuit 29 and matrix circuits $19K_1-19K_4$ and the procedure by the microprocessor 26 which controls the adder/switching circuit and matrix circuits. These adder/switching circuit, matrix circuits and microprocessor are shown in FIG. 9. The remaining elements are the same as the corresponding elements in the preceding embodiment. A description will therefore be made of an adder circuit 29' and matrix circuits $19K_{1'}-19K_{4'}$ in the present embodiment, which correspond to the adder/switching circuit 29 and matrix circuits $19K_1-19K_4$ in the preceding embodiment.

Figure 13:
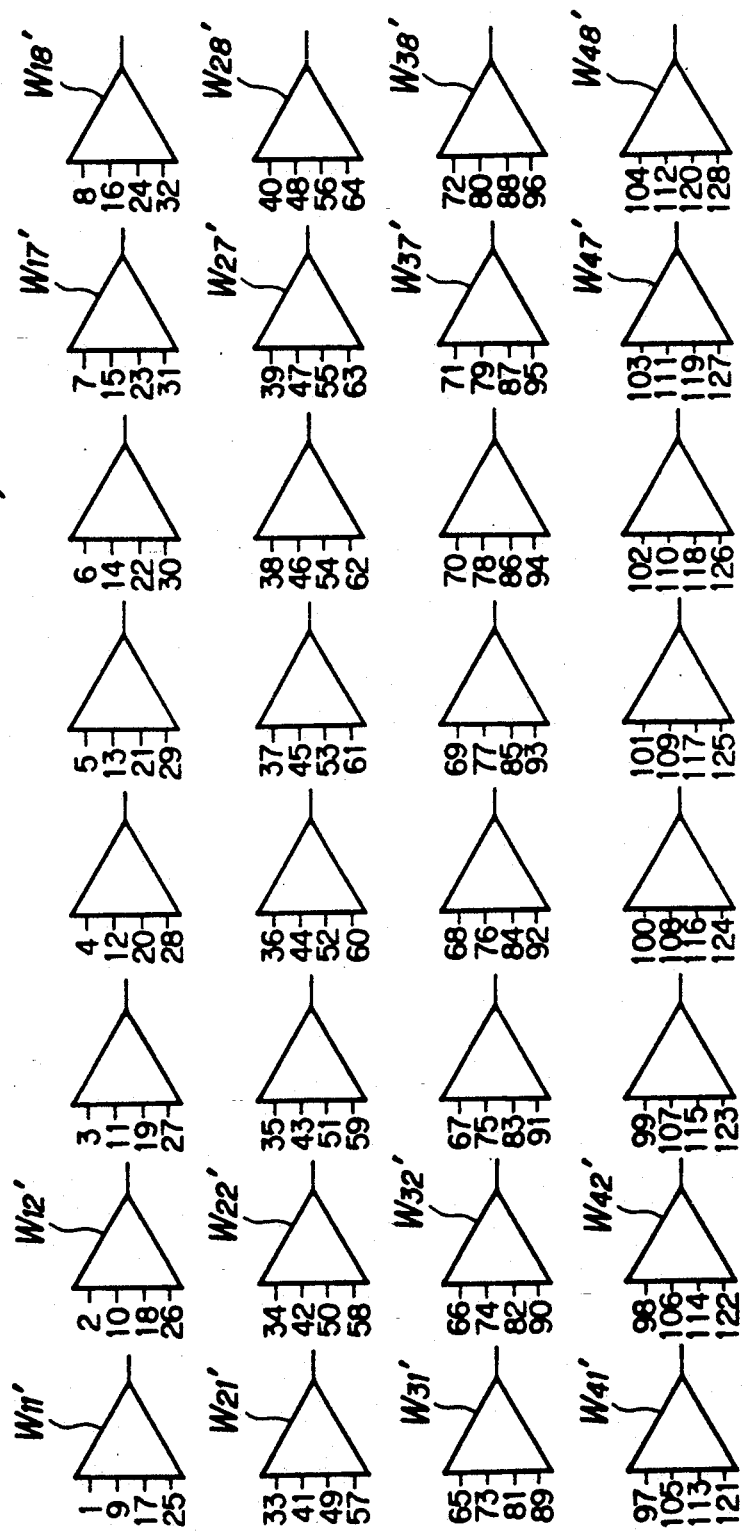
FIG. 13 is a circuit diagram of an adder of an ultrasonic flaw detector according to another embodiment of the present invention.

FIG. 13 is a circuit diagram of the adder circuit 29'. In the drawing, numerals 1–128 indicate the numbers of input terminals of the adder circuit 29' and symbols $W_{11'}$–$W_{48'}$ designate adders. The adder circuit 29' is different from the adder/switching circuit 29 in the preceding embodiment in that the adders $W_{11}$–$W_{48}$ in the preceding embodiment individually have five input terminals and the adjacent input terminals of each two adjacent adders are changed over by the switch S while the adders $W_{11'}$–$W_{48'}$ in this embodiment individually have four input terminals and have neither switches S nor terminals to be changed over by such switches. Accordingly, signals from the transmit/receive circuit 27 are simply and successively inputted to the individual terminals in the four blocks.

FIGS. 14(a), 14(b), 14(c) and 14(d) are circuit diagrams of the matrix circuits $19K_{1'}$–$19K_{4'}$. The matrix circuit $19K_{1'}$ comprises two matrix switches $19K_{11'},19K_{12'}$, whereas the matrix circuit $19K_{2'}$ comprises two matrix switches $19K_{21'},19K_{22'}$. Further, the matrix circuit $19K_{3'}$ comprises two matrix switches $19K_{31'},19K_{32'}$, whereas the matrix circuit $19K_{4'}$ comprises two matrix switches $19K_{41'},19K_{42'}$. Output terminals of the adders $W_{11'}$–$W_{18'}$ shown in FIG. 13 are connected to the matrix switch $19K_{11'}$, and output terminals of the adders $W_{21'}$–$W_{28'}$ are connected both the matrix switch $19K_{12'}$, and the matrix switch $19K_{21'}$. Furthermore, output terminals of the adders $W_{31'}$–$W_{38'}$ are connected to both the matrix switch $19K_{22'}$ and the matrix switch $19K_{31'}$, and output terminals of the adders $W_{41'}$–$W_{48'}$ are connected to both the matrix switch $19K_{32'}$ and the matrix switch $19K_{41'}$. The matrix switch $19K_{42'}$ is a dummy switch which will not be used. Output lines of the matrix circuits $19K_{1'}$–$19K_{4'}$ are common to the associated two matrix switches and are connected to waveform adders $20K_1$–$20K_4$.

Next, the operation of this embodiment will be described. In FIG. 14(a), the 1st–8th terminals of the adders $W_{11'}$–$W_{18'}$, the 33rd–40th terminals of the adders $W_{21'}$–$W_{28'}$, the 65th–72nd terminals of the adders $W_{31'}$–$W_{38'}$ and the 97th–104th terminals of the adders $W_{31'}$–$W_{38'}$, all the adders being shown in FIG. 13, have been inputted with signals, respectively. In this state, the matrix switches at the crossing points indicated by circles out of the individual matrix switches are closed. Signals appeared at the individual terminals are inputted to the waveform addition circuits $20K_1$–$20K_4$, respectively. Namely, signals of reflected waves of the ultrasonic beams $B_1,B_{33},B_{65},B_{97}$ depicted in FIG. 10 are obtained at the respective waveform addition circuits $20K_1$–$20K_4$.

When the transmit-receive circuit 27 is switched and shifted by the shift register 28 subsequent to the above state, the state of signal inputs to the respective matrix circuits $19K_{1'}$–$19K_{4'}$ becomes as shown in FIG. 14(b). At this time, the state of closure of each individual matrix switch is as indicated by a circle. As a result, data on reflected waves of the next ultrasonic beams in the respective blocks are obtained at the waveform addition circuits $20K_1$–$20K_4$, respectively.

In the manner described above, the individual matrix switches $19K_{11'},19K_{21'},19K_{31'},19K_{41'}$ are successively changed over to obtain individual reflected wave data. When the first array elements $10_{33},10_{65},10_{97}$ in the boundary sections $K_{12},K_{23},K_{34}$ depicted in FIG. 10 become ready for use again, in other words, the 33rd, 65th and 97th terminals shown in FIG. 13 are brought into a signal-inputted state again, one switches of the matrix switches $19K_{12'},19K_{22'},19K_{32'},19K_{42'}$ of the individual matrix circuits $19K_{1'}$–$19K_{4'}$, said one switches corresponding respectively to the above terminals, are brought into a closed state as indicated by circles in FIG. 14(c). Thereafter, the vibration of the array elements in the respective boundary sections $K_{12}$–$K_{34}$ is shifted one element by one element and at the same time, the closure of crossing points of one matrix switches $19K_{11'}$–$19K_{41'}$ is shifted one crossing point by one crossing point toward the other matrix switches $19K_{11'}$–$19K_{41'}$. In this manner, the formation of ultrasonic beams by the use of the array elements of the boundary sections $K_{12}$–$K_{34}$ is shifted successively. Upon formation of the last ultrasonic beams, the state of closure of the respective matrix switches is as indicated by circles in FIG. 14(d). Namely, in each of one matrix switches $19K_{11'},19K_{21'},19K_{31'}, 19_{41'}$, only one crossing point is in a closed state. In each of the other matrix switches $19K_{12'},19K_{22'},19K_{32'}.19K_{42'}$, seven closed states are formed.

Omission of ultrasonic beams can be prevented by forming two matrix switched in the matrix circuit as described above, thereby bringing about the same effects as the preceding embodiment. Moreover, the construction of the adder circuit 29' can be simplified in this embodiment. Owing to this, the adders $W_{11'}$–$W_{18'}$, $W_{21'}$–$W_{28'}$, $W_{31'}$–$W_{38'}$, $W_{41'}$–$W_{48'}$ can be fabricated as discrete integrated circuits so that the fabrication can be facilitated.

Figure 7:
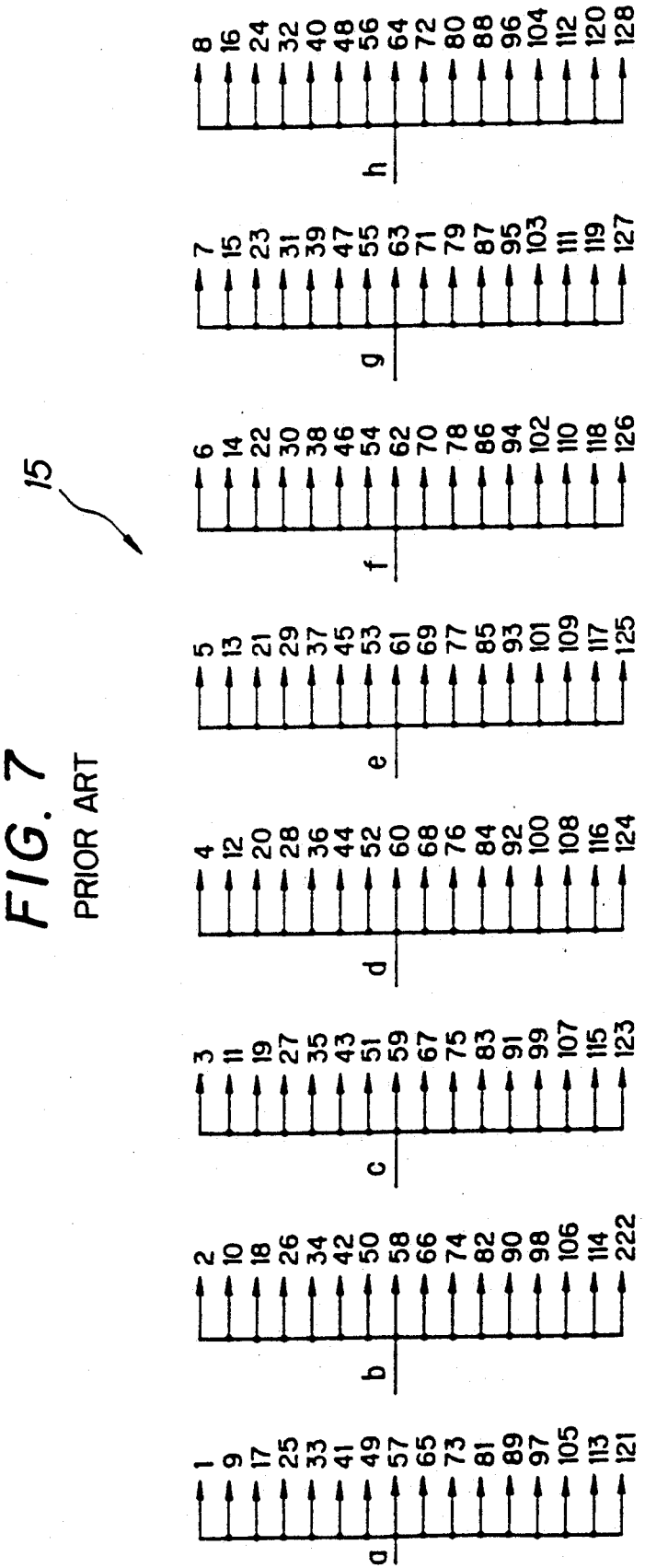
Figure 8:
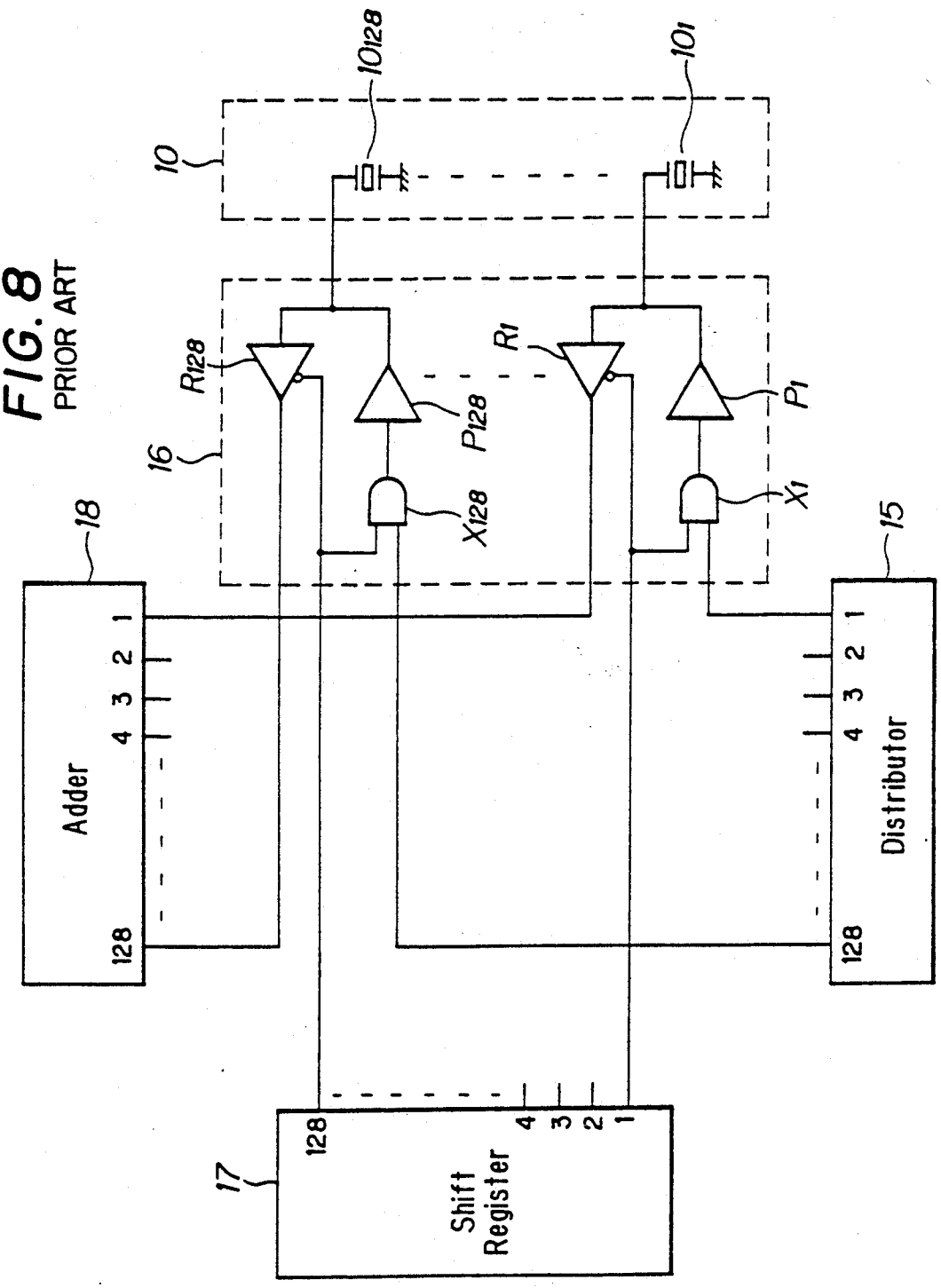

In the description of each of the above embodiments, array elements were arranged, as an array probe, in a straight line by way of example. The array elements are not limited to such arrangements. They may be arranged in plural lines. In such case, each line can be provided with a control unit. As an alternative, the circuit constructions of the shift register and the circuit constructions of the adder/switching circuit and the subsequent circuits can be modified. When a specimen has a curved surface or where the points of inspection targets are on a curved surface, array elements may be arranged in a pattern extending along the curved surface rather than in a straight line. Where the curved surface is a simple curved surface, the array elements may be arranged in a straight line provided that the setting of delay times is modified by a microprocessor to conform with the curved surface. Electronic switching elements are of course used as the switches in the adder/switching circuit. It is necessary to perform their change-over after an input to the last input terminal of the input terminals of each intermediate section is completed but before an input next takes place to the first input terminal. In the above embodiments, adders were used in the adder/switching circuits. They were employed in view of impedance matching. Where it is unnecessary to take impedance matching into account, the simple connection shown in FIG. 7 can be used.

In the above description, the sampling pitch of ultrasonic scanning was set equal to the pitch of arrangement of the array elements to facilitate the understanding. In order to make the sampling pitch still finer, there have however been adopted a means for selecting array elements, which take part in the formation of a beam, in varied combinations such that the even-numbered array elements are first selected and the odd-numbered array elements are then selected; and a means for varying the number of array elements which take part upon transmission of an ultrasonic beam and reception or selecting such array elements in different combinations. These means have been well known in the art. It is apparent that these means can also be incorporated in detectors according to the present invention.

As has been described above, the array elements are divided into plural blocks, and the input terminals of the input/output unit are also divided into blocks corresponding to the first-mentioned blocks and intermediate sections corresponding to the boundaries of the first-mentioned blocks. The individual input terminals in each intermediate section can be caused to belong to both of the associated adjacent blocks by a switching means. The present invention can therefore substantially shorten the time of electronic scanning making use of ultrasonic beams and accordingly, to significantly improve the inspection speed.

We claim:

1. An ultrasonic flaw detector, said ultrasonic flaw detector comprising:

an array probe formed of a number of array elements arranged in a line, the array elements being divided into plural blocks with groups of some of said array elements overlapping between adjacent ones of the plural blocks;

pulses for feeding delay pulses to plural ones of the array elements to vibrate the plural array elements; and receivers for receiving signals of reflected waves of an ultrasonic beam by the plural array elements, vibration of said array elements being successively shifted to conduct scanning by ultrasonic beams;

each of the blocks being provided with block selecting means for selecting plural ones of the array elements in the same block and shifting vibration of the array elements in the same block, a plurality of connector means each having plural input terminals and one output terminal, said plural input terminals of each connector means receiving output signals from said receivers corresponding with two or more of said array elements which are vibrated successively, a matrix circuit for delaying signals which had been outputted from the output terminals of the respective connector means in the block, in the same delay modes as the delays of the corresponding delay pulses, respectively, switching means for causing output signals which had been fed from said receivers connected to the respective array elements in the overlapping group to selectively belong to one of the adjacent blocks or to the other one of the adjacent blocks, and means for adding delayed outputs via the matrix circuit.

2. The ultrasonic flaw detector of claim 1, wherein said switching means selectively switches over output signals which had been fed from the receivers connected to the individual array elements in the overlapping group to the input terminals of the connector means of one of the adjacent blocks or to the input terminals of the connector means of the other one of the adjacent blocks.

3. The ultrasonic flaw detector of claim 1, wherein said switching means causes the output terminals of the plural connector means which have the input terminals to which output signals from the receivers connected to the respective array elements in the overlapping group are inputted to belong to both the matrix circuits of the respective adjacent blocks and, when output signals from the receivers connected to the respective array elements in the overlapping group have been outputted from the output terminals of the connector means, delivers the individual output signals to the matrix circuits on the side of predetermined one of the adjacent blocks.

* * * * *